United States Patent
Ren et al.

(10) Patent No.: US 7,659,444 B2
(45) Date of Patent: Feb. 9, 2010

(54) COMPOSITIONS AND METHODS USING RNA INTERFERENCE FOR CONTROL OF NEMATODES

(75) Inventors: Peifeng Ren, Cary, NC (US); Xiang Huang, Apex, NC (US); Sumita Chaudhuri, Cary, NC (US); Lawrence Talton, Sanford, NC (US); John McMillan, Raleigh, NC (US)

(73) Assignee: BASF Plant Science GmbH (DE)

( * ) Notice: Subject to any disclaimer, the term of this patent is extended or adjusted under 35 U.S.C. 154(b) by 0 days.

(21) Appl. No.: 11/161,691

(22) Filed: Aug. 12, 2005

(65) Prior Publication Data

US 2006/0037101 A1 Feb. 16, 2006

Related U.S. Application Data

(60) Provisional application No. 60/601,327, filed on Aug. 13, 2004.

(51) Int. Cl.
*C12N 15/09* (2006.01)
*C12N 15/82* (2006.01)
*A01H 5/00* (2006.01)

(52) U.S. Cl. .................. 800/279; 800/278; 800/298; 800/312; 800/286; 800/288; 435/320.1; 435/468; 435/430

(58) Field of Classification Search .................. None
See application file for complete search history.

(56) References Cited

U.S. PATENT DOCUMENTS

| | | | |
|---|---|---|---|
| 5,589,622 A | 12/1996 | Gurr et al. | 800/205 |
| 5,824,876 A | 10/1998 | Gurr et al. | 800/205 |
| 6,506,559 B1 | 1/2003 | Fire et al. | 435/6 |
| 6,521,438 B1 | 2/2003 | Davis et al. | |
| 6,784,337 B1 | 8/2004 | Atkinson et al. | |
| 2002/0086356 A1 | 7/2002 | Tuschl et al. | |
| 2005/0091713 A1 | 4/2005 | Atkinson et al. | |

FOREIGN PATENT DOCUMENTS

| | | |
|---|---|---|
| EP | 0983370 B1 | 9/2003 |
| WO | WO 99/53050 | 10/1999 |
| WO | WO 01/96584 A2 | 12/2001 |
| WO | 2004005485 A2 | 1/2004 |

OTHER PUBLICATIONS

Hussey et al. Braz. J. Plant Physiol., 14(3): 183-194 (2002).*
Atkinson et al. Annual Rev. Phytopathology (2003), vol. 41:615-639.*
Thomas et al. The Plant Journal (2001) 25(4), pp. 417-425.*
Brenda Bass, Cell (2000) 101:235-238.*
Elbashir et al. Gene and Development (2001) 15:188-200.*
Darmacon RNA Technologies (2004), 1$^{st}$ edition, RNA Intterference, Technical Reference and Application Guide, pp. 9-11.*
Hammond et al., "Post-transcriptional gene silencing by double-stranded RNA," Nature Reviews, Feb. 2001, pp. 110-119, vol. 2.
Bass, BL, "Double-stranded RNA as a template for gene silencing," Cell, Apr. 28, 2000, pp. 235-238, vol. 101.
Elbashir et al., "Duplexes of 21-nucleotide RNAs mediate RNA interference in cultured mammalian cells," Nature, May 24, 2001, pp. 494-498, vol. 411.
Bass, BL, "The short answer," Nature, May 24, 2001, pp. 428-429, vol. 411.
Young LD, "Managing soybean resistance to heterodera glycines," Suppl. to Journal of Nematology, 1998, pp. 525-529, vol. 30:4S.
Davis et al., "Nematode parasitism genes," Annu. Rev. Phytopathol., Sep. 2000, pp. 341-372, vol. 38.
Boutla et al., "Induction of RNA interference in Caenorhabditis elegans by RNAs derived from plants exhibiting . . . ," Nucleic Acids Res., 2002, pp. 1688-1694, 30:7.
Urwin et al., "Ingestion of double-stranded RNA by preparasitic juvenile cyst nematodes leads to RNA interference,"MPMI, 2002, pp. 747-752, 15:8.
David P. Bartel, "MicroRNAs: Genomics, Biogenesis, Mechanism, and Function", journal, Jan. 23, 2004, Cell, vol. 116, 281-297, Cell Press, Cambridge, Massachusetts.
Yukio Kurihara and Yuichiro Watanabe, "Arabidopsis micro-RNA biogenesis through Dicer-like 1 protein functions", journal, Aug. 24, 2004, 12753-12758, vol. 101, No. 34 PNAS.
Anne Davy et al., "A protein-protein interaction map of the Caenorhabditis elegans 26S proteasome,"EMBO Reports, 2001, pp. 821-828, 21:91.
Bingli Gao et al., "Identification of Putative Parasitism Genes Expressed in the Esophageal Gland Cells of the Soybean Cyst Nematode Heterodera glycines," MPMI, 2001, pp. 1247-1254, 14:10 duplicate of the IDS of Aug. 14, 2009.
Ryan M. Steeves et al., "Utilization of RNA Interference to Confer Resistance to the Soybean Cyst Nematode, Heterodera glycines," In Vitro Cellular and Developmental Biology Plant, Apr. 2003, pp. 23-A, 39(Abs).
Maiko Takahashi et al., "Reverse Genetic Analysis of the Caenorhabditis elegans 26S Proteasome Subunits by RNA Interference," Biol. Chem., Jul./Aug. 2002, pp. 1263-1266, vol. 383.
Bingli Gao, at al., "Identification of Putative Parasitism Genes Expressed in the Esophageal Gland Cells of the Soybean Cyst Nematode Heterodera glycines" Molecular Plant-Microbe Interactions, vol. 14, No. 10, 2001, pp. 1247-1254.

* cited by examiner

*Primary Examiner*—Medina A Ibrahim
(74) *Attorney, Agent, or Firm*—Patricia A. McDaniels

(57) ABSTRACT

The present invention concerns double stranded RNA compositions and transgenic plants capable of inhibiting expression of essential genes in parasitic nematodes, and methods associated therewith. Specifically, the invention relates to the use of RNA interference to inhibit expression of a target essential parasitic nematode gene, which is a parasitic nematode pas-5 gene, and relates to the generation of plants that have increased resistance to parasitic nematodes.

20 Claims, 4 Drawing Sheets

SEQ ID NO:1

(H. glycines pas-5 full-length cDNA)

gaaaacaacgtttctacttttacttctgaatctataagtactacttccctattttaaaataataattattaagtg
aattttcgacttacctataaatgtttctgacccgcagcgaatacgacaggggagtgaacactttttccccggagg
gccgtctgttccaagtggaatatgccatcgaaactgtcaagcttggttccacaagcatcggaattcacaccaaag
aaggcgttcttttggctgcggaaaggcgttcaatgagcaaattggtggtggacgactcaatgagcaaaatttcgg
aagttgagaagcacattgccgtcgcctcggccggtctcatcgcagattcacgcacttgggtcgaacacgcgcggg
tggaggctcaacacttttggtttacttacggtggcaaaattcgggtggaagacattactcaaaaggtctcaagat
tggcactgcattttggagacgacgactcaactatcagtctcggccgtccgtttggagtttctatgctttttgccg
gcattgatcacacgggtgcgcatctcttccatttggacccgtccgggacgtacattaaatgtttggccgaggcca
tcggtgccggctccgatgcagcggaacaaacgctgcaagagcactgtaaaaactgcgacaaaaaaatggaaatgg
ccgaggcaaaacaagtcgcactgaacacactcaaacaactgatggaagagaaaatcaattccaaaaatgtggaaa
ttgttatgattaagccgcagacggacaaggaaggcaaaacgttgggcaaaattgtgtggttagaggaatcggagt
tgcaagaaatcatttcgcgattgtagtcgaaggggacggattagagaaggaaaatgggctttgcactgccccttt
tatgattggatgaccttttgttattctctgcctttttgtgacttttcagtgtataaggcaaatgaaagcaattaa
ttg

FIGURE 1

| Common Primers | SEQ ID NO | |
|---|---|---|
| SL1 | 2 | GGTTTAATTACCCAAGTTTGA |
| GeneRacer 5' Primer | 3 | CGACTGGAGCACGAGGACACTGA |
| GeneRacer 5' Nested Primer | 4 | GGACACTGACATGGACTGAAGGAGTA |
| GeneRacer 3' Primer | 5 | GCTGTCAACGATACGCTACGTAACG |
| GeneRacer 3' Nested Primer | 6 | CGCTACGTAACGGCATGACAGTG |
| GeneRacer Oligo dT | 7 | GCTGTCAACGATACGCTACGTAACGGCATGACAGTG(T)$_{24}$ |

| Gene | SEQ ID NO | Forward Primer | SEQ ID NO | Reverse Primer |
|---|---|---|---|---|
| H. glycines pas-5 middle | 8 | GTGAATTTTCGACTTACCTA | 9 | AAACATTTAATGTACGTCCC |
| H. glycines pas-5 5' | 3 | GeneRacer 5' Primer | 10 | GAGGCGACGGCAATGTGCTTCTCAA |
| H. glycines pas-5 5' nested | 4 | GeneRacer 5' Nested Primer | 11 | GCTCATTGAGTCGTCCACCACCAA |
| H. glycines pas-5 3' | 12 | GGTCTCATCGCAGATTCACGCACTT | 5 | GeneRacer 3' Primer |
| H. glycines pas-5 3' nested | 13 | GGAGACGACGACTCAACTATCAGT | 6 | GeneRacer 3' Nested Primer |
| Ce F25H2.9 | 14 | CGACTATCCCACCTCTTCCA | 15 | GTGCGGACGTATTGAATGTG |

FIGURE 2

SEQ ID NO: 16

(*C. elegans* homolog of *H. glycines pas-5*)

cgactatcccacctcttccattttttttgtgcttcaatatgtccaatgttgcttcgaatataatttatttacatttcagccagtcatgttcctca
ctcgcagcgagtacgatcgtggagtcaacactttttctccagaagggcgtttgttccaagtggaatacgctattgaggccgtcaaa
ctcggatctacaagcattggaatcaagacgagcgaaggtgttcttctcgctgctgagaaaagatcgacatcgaagctgatggtca
atgacgcgatcgagaaaatcagcaaggtcgaccaacatattggttagttctgtgaactgtttatcatcttaatttataagaattgtttca
ggcgtcacattcgcaggtttgattgccgactcgcgcactctggtcgaacgggcacagatcgaggctcaaaatttctggttcactta
taaccgcaaaattcgcgtggaagacgtcactcagtcggtcgccaatctagctcttcagtttggagacgacgacgtcaaagcatca
atgtctcgtccatttggtgtagcaatgctgttcgctggtgtagaccaagaaggagccaaactgttccatctcgatccatctggaactt
tcatcgattgtaaggctaaatcgatcggtgcagctagcgatggagctgagcagaatctcaaggagcaatatcatgatgtaatttcg
tcaaatatggttatacaggaaaatgtattttatttcaggctctgactatcaaggaaggactcaagatggcattggccattctcaagca
ggtgatggaagagaaactgaactccgccaatgtcgaagtcgttgttatcaaaccaacagttgacgcgaaggggcgtccaatcg
gagaattcacaagagtgtcgaacgaagagctcgatcaagttatcacatcgctttgaagaaattattctttcctggttttttgtctcttgtt
tcttatggtgtaaagtaactttatttgcgatgttcagctatttcaataaattatttgtcgttcttttatacattttttgaaagcgccacacattc
aatacgtccgcac

FIGURE 3

SEQUENCE LISTING

<160> NUMBER OF SEQ ID NOS: 16

<210> SEQ ID NO 1
<211> LENGTH: 978
<212> TYPE: DNA
<213> ORGANISM: Heterodera glycines

<400> SEQUENCE: 1

```
gaaaacaacg tttctacttt tacttctgaa tctataagta ctacttccct attttaaaat      60
aataattatt aagtgaattt tcgacttacc tataaatgtt tctgacccgc agcgaatacg     120 acagggagt gaacactttt tccccggagg gccgtctgtt ccaagtggaa tatgccatcg      180
aaactgtcaa gcttggttcc acaagcatcg gaattcacac caaagaaggc gttcttttgg     240
ctgcggaaag gcgttcaatg agcaaattgg tggtggacga ctcaatgagc aaaatttcgg     300
aagttgagaa gcacattgcc gtcgcctcgg ccggtctcat cgcagattca cgcacttggg     360
tcgaacacgc gcgggtggag gctcaacact tttggtttac ttacggtggc aaaattcggg     420
tggaagacat tactcaaaag gtctcaagat tggcactgca ttttggagac gacgactcaa     480
ctatcagtct cggccgtccg tttggagttt ctatgctttt tgccggcatt gatcacacgg     540
gtgcgcatct cttccatttg gacccgtccg ggacgtacat taaatgtttg gccgaggcca     600
tcggtgccgg ctccgatgca gcggaacaaa cgctgcaaga gcactgtaaa aactgcgaca     660
aaaaaatgga aatggccgag gcaaaacaag tcgcactgaa cacactcaaa caactgatgg     720
aagagaaaat caattccaaa aatgtggaaa ttgttatgat taagccgcag acggacaagg     780
aaggcaaaac gttgggcaaa attgtgtggt tagaggaatc ggagttgcaa gaaatcattt     840
cgcgattgta gtcgaagggg acggattaga gaaggaaaat gggctttgca ctgccccttt     900
tatgattgga tgacctttg ttattctctg ccttttttgtg acttttcagt gtataaggca     960
aatgaaagca attaattg                                                   978
```

<210> SEQ ID NO 2
<211> LENGTH: 21
<212> TYPE: DNA

```
<213> ORGANISM: Artificial Sequence
<220> FEATURE:
<223> OTHER INFORMATION: Description of Artificial Sequence: Synthetic
      primer

<400> SEQUENCE: 2
ggtttaatta cccaagtttg a                                              21

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
cgactggagc acgaggacac tga                                            23

<210> SEQ ID NO 4
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ggacactgac atggactgaa ggagta                                         26

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gctgtcaacg atacgctacg taacg                                          25

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
cgctacgtaa cggcatgaca gtg                                            23

<210> SEQ ID NO 7
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gctgtcaacg atacgctacg taacggcatg acagtgtttt ttttttttt ttttttttt      60

<210> SEQ ID NO 8
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 8
gtgaattttc gacttaccta                                                      20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
aaacatttaa tgtacgtccc                                                      20

<210> SEQ ID NO 10
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gaggcgacgg caatgtgctt ctcaa                                                25

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gctcattgag tcgtccacca ccaa                                                 24

<210> SEQ ID NO 12
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ggtctcatcg cagattcacg cactt                                                25

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ggagacgacg actcaactat cagt                                                 24
```

```
<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
cgactatccc acctcttcca                                                    20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
gtgcggacgt attgaatgtg                                                    20

<210> SEQ ID NO 16
<211> LENGTH: 1069
<212> TYPE: DNA
<213> ORGANISM: Caenorhabditis elegans

<400> SEQUENCE: 16
cgactatccc acctcttcca ttttttttgtg cttcaatatg tccaatgttg cttcgaatat       60
aatttattta catttcagcc agtcatgttc ctcactcgca gcgagtacga tcgtggagtc      120 aacactttt ctccagaagg gcgtttgttc caagtggaat acgctattga ggccgtcaaa      180
ctcggatcta caagcattgg aatcaagacg agcgaaggtg ttcttctcgc tgctgagaaa      240
agatcgacat cgaagctgat ggtcaatgac gcgatcgaga aaatcagcaa ggtcgaccaa      300
catattggtt agttctgtga actgtttatc atcttaattt ataagaattg tttcaggcgt      360
cacattcgca ggtttgattg ccgactcgcg cactctggtc gaacgggcac agatcgaggc      420
tcaaaatttc tggttcactt ataaccgcaa aattcgcgtg gaagacgtca ctcagtcggt      480
cgccaatcta gctcttcagt ttggagacga cgacgtcaaa gcatcaatgt ctcgtccatt      540
tggtgtagca atgctgttcg ctggtgtaga ccaagaagga gccaaactgt tccatctcga      600
tccatctgga actttcatcg attgtaaggc taaatcgatc ggtgcagcta gcgatggagc      660
tgagcagaat ctcaaggagc aatatcatga tgtaatttcg tcaaatatgg ttatacagga      720
aaatgtattt tatttcaggc tctgactatc aaggaaggac tcaagatggc attggccatt      780
ctcaagcagg tgatggaaga gaaactgaac tccgccaatg tcgaagtcgt tgttatcaaa      840
ccaacagttg acgcgaaggg gcgtccaatc ggagaattca caagagtgtc gaacgaagag      900
ctcgatcaag ttatcacatc gctttgaaga aattattctt tcctggtttt ttgtctcttg      960
tttcttatgg tgtaaagtaa ctttatttgc gatgttcagc tatttcaata aattatttgt     1020
cgttctttta tacatttttg aaagcgccac acattcaata cgtccgcac                 1069
```

COMPOSITIONS AND METHODS USING RNA INTERFERENCE FOR CONTROL OF NEMATODES

CROSS-REFERENCE TO RELATED APPLICATIONS

The present application claims the priority benefit of U.S. Provisional Patent Application Ser. No. 60/601,327, filed Aug. 13, 2004, the entire contents of which application are hereby incorporated by reference.

BACKGROUND OF THE INVENTION

1. Field of the Invention

The field of this invention is the control of nematodes, in particular the control of soybean cyst nematodes. The invention also relates to the introduction of genetic material into plants that are susceptible to nematodes in order to increase resistance to nematodes.

2. Background Art

Nematodes are microscopic wormlike animals that feed on the roots, leaves, and stems of more than 2,000 vegetables, fruits, and ornamental plants, causing an estimated $100 billion crop loss worldwide. One common type of nematode is the root-knot nematode, whose feeding causes the characteristic galls on roots. Other root-feeding nematodes are the cyst- and lesion-types, which are more host specific.

Nematodes are present throughout the United States, but are mostly a problem in warm, humid areas of the South and West, and in sandy soils. Soybean cyst nematode (SCN), *Heterodera glycines*, was first discovered in the United States in North Carolina in 1954. It is the most serious pest of soybean plants. Some areas are so heavily infested by SCN that soybean production is no longer economically possible without control measures. Although soybean is the major economic crop attacked by SCN, SCN parasitizes some fifty hosts in total, including field crops, vegetables, ornamentals, and weeds.

Signs of nematode damage include stunting and yellowing of leaves, and wilting of the plants during hot periods. However, nematodes, including SCN, can cause significant yield loss without obvious above-ground symptoms. In addition, roots infected with SCN are dwarfed or stunted. SCN can decrease the number of nitrogen-fixing nodules on the roots, and may make the roots more susceptible to attacks by other soil-borne plant pathogens.

The SCN life cycle has three major stages: egg, juvenile, and adult. The life cycle can be completed in 24 to 30 days under optimum conditions. When temperature and moisture levels become adequate in the spring, worm-shaped juveniles hatch from eggs in the soil. These juveniles are the only life stage of the nematode that can infect soybean roots.

After penetrating the soybean roots, juveniles move through the root until they contact vascular tissue, where they stop and start to feed. The nematode injects secretions that modify certain root cells and transform them into specialized feeding sites. The root cells are morphologically transformed into large multinucleate syncytia or giant cells, which are used as a source of nutrients for the nematodes. The actively feeding nematodes thus steal essential nutrients from the plant resulting in yield loss. As the nematodes feed, they swell and eventually female nematodes become so large that they break through the root tissue and are exposed on the surface of the root.

Male nematodes, which are not swollen as adults, migrate out of the root into the soil and fertilize the lemon-shaped adult females. The males then die, while the females remain attached to the root system and continue to feed. The swollen females begin producing eggs, initially in a mass or egg sac outside the body, then later within the body cavity. Eventually the entire body cavity of the adult female is filled with eggs, and the female nematode dies. It is the egg-filled body of the dead female that is referred to as the cyst. Cysts eventually dislodge and are found free in the soil. The walls of the cyst become very tough, providing excellent protection for the 200 to 400 eggs contained within. SCN eggs survive within the cyst until proper hatching conditions occur. Although many of the eggs may hatch within the first year, many also will survive within the cysts for several years.

SCN can move through the soil only a few inches per year on its own power. However, SCN can be spread substantial distances in a variety of ways. Anything that can move infested soil is capable of spreading SCN, including farm machinery, vehicles and tools, wind, water, animals, and farm workers. Seed sized particles of soil often contaminate harvested seed. Consequently, SCN can be spread when seed from infested fields is planted in non-infested fields. There is even evidence that SCN can be spread by birds. Only some of these causes can be prevented.

Traditional practices for managing SCN include: maintaining proper fertility and soil pH levels in SCN-infested land; controlling other plant diseases, as well as insect and weed pests; using sanitation practices such as plowing, planting, and cultivating of SCN-infested fields only after working non-infested fields; cleaning equipment thoroughly with high pressure water or steam after working in infested fields; not using seed grown on infested land for planting non-infested fields unless the seed has been properly cleaned; rotating infested fields and alternating host crops with non-host crops, such as, corn, oat and alfalfa; using nematicides; and planting resistant soybean varieties.

Methods have been proposed for the genetic transformation of plants in order to confer increased resistance to plant parasitic nematodes. U.S. Pat. Nos. 5,589,622 and 5,824,876 are directed to the identification of plant genes expressed specifically in or adjacent to the feeding site of the plant after attachment by the nematode. The promoters of these plant target genes can then be used to direct the specific expression of toxic proteins or enzymes, or the expression of antisense RNA to the target gene or to general cellular genes. The plant promoters may also be used to confer cyst nematode resistance specifically at the feeding site by transforming the plant with a construct comprising the promoter of the plant target gene linked to a gene whose product induces lethality in the nematode after ingestion. However, these patents do not provide any specific nematode genes that are useful for conferring resistance to nematode infection, and the methods are only useful for expressing genes specifically at the feeding sites for nematodes after attachment to the plant.

Recently, RNA interference (RNAi), also referred to as gene silencing, has been proposed as a method for controlling nematodes. When double-stranded RNA (dsRNA) corresponding essentially to the sequence of a target gene or mRNA is introduced into a cell, expression from the target gene is inhibited (See e.g., U.S. Pat. No. 6,506,559). U.S. Pat. No. 6,506,559 demonstrates the effectiveness of RNAi against known genes in *C. elegans*, but does not teach or suggest any novel genes that are essential for plant parasitic nematodes, and does not demonstrate the usefulness of RNAi for controlling plant parasitic nematodes.

In addition, RNAi was used in PCT Publication WO 01/96584 to target nematode genes, preferably in root-knot nematodes and potato cyst nematodes. Preferred targets included molecules involved in ribosome assembly; neurotransmitter receptors and ligands; electron transport proteins; metabolic pathway proteins; and proteins involved in protein and polynucleotide production, folding, and processing. However, none of the sequences provided in PCT Publication WO 01/96584 were demonstrated to be down-regulated using RNAi, and moreover, they were not shown to be useful in conferring resistance to plant parasitic nematodes.

PCT Publication WO 01/17654 A2 also proposed the use of RNAi for targeting essential plant pathogenic and parasitic nematode genes. The host plant is preferably transformed with a construct for expressing dsRNA that has substantial sequence identity to an endogenous and essential nematode gene. The publication proposes that the invention is particularly useful for targeting a vascular acetylcholine transporter protein, a choline acetyltransferase, and a ubiquinone oxidoreductase. WO 01/17654 demonstrated that RNAi was effective in reducing expression of sec-1, involved in vesicle trafficking, in *Meloidogyne incognita*. However, sec-1 was not shown to be essential for plant parasitic nematodes or useful for conferring plant resistance to nematodes, and the patent publication does not teach or suggest any novel genes that are essential for plant parasitic nematodes.

A number of models have been proposed for the action of RNAi. See, e.g., Hammond et al. (2001) *Nature Reviews Genetics* 2, 110-119, and references cited therein. In mammalian systems, dsRNAs larger than 30 nucleotides trigger induction of interferon synthesis and a global shut-down of protein syntheses, in a non-sequence-specific manner. See, e.g., Bass (2001) *Nature* 411, 428-429; Elbashir, et al. (2001) *Nature* 411, 494-498. However, U.S. Pat. No. 6,506,559 discloses that in nematodes, the length of the dsRNA corresponding to the target gene sequence may be at least 25, 50, 100, 200, 300, or 400 bases, and that even larger dsRNAs (742 nucleotides, 1033 nucleotides, 785 nucleotides, 531 nucleotides, 576 nucleotides, 651 nucleotides, 1015 nucleotides, 1033 nucleotides 730 nucleotides, 830 nucleotides, see Table 1) were also effective at inducing RNAi in *C. elegans*. Moreover, Wesley, et al. (2001) *The Plant Journal* 27, 581-590 discloses that when hairpin RNA constructs comprising double stranded regions ranging from 98 to 854 nucleotides were transformed into a number of plant species, the target plant genes were efficiently silenced. There is general agreement that in many organisms, including nematodes and plants, large pieces of dsRNA are cleaved into 21-23 nucleotide fragments (siRNA) within cells, and that these siRNAs are the actual mediators of the RNAi phenomenon.

Notwithstanding the foregoing, there is a need to identify safe and effective compositions and methods for the controlling plant parasitic nematodes using RNAi, and for the production of plants having increased resistance to plant parasitic nematodes.

SUMMARY OF THE INVENTION

The present invention provides nucleic acids, transgenic plants, and methods to overcome, or at least alleviate, nematode infestation of valuable agricultural crops such as soybeans. The nucleic acids of the invention are capable of modulating expression of parasitic nematode target genes by RNA interference (RNAi). In accordance with the invention, the parasitic nematode target gene is a parasitic nematode pas-5 gene. The nucleic acid of the invention encodes a double stranded RNA comprising (a) a first strand comprising a sequence substantially identical to from about 21 to about 400 or 500 consecutive nucleotides of a target gene having a sequence as set forth in SEQ ID NO:1 and (b) a second strand comprising a sequence substantially complementary to the first strand.

The invention is further embodied as a pool of double stranded RNA molecules comprising a multiplicity of short interfering RNA molecules each comprising a double stranded region having a length of about 21 nucleotides, wherein said RNA molecules are derived from a polynucleotide selected from the group consisting of (a) a polynucleotide having a sequence as set forth in SEQ ID NO:1; and (b) a polynucleotide from a parasitic nematode that hybridizes under stringent conditions to a polynucleotide having a sequence as set forth in SEQ ID NO:1.

In another embodiment, the invention provides a transgenic plant resistant to parasitic nematode infection, the plant comprising a nucleic acid construct that encodes a dsRNA capable of specifically modulating a parasitic nematode pas-5 target gene.

In another embodiment, the invention provides a method for controlling the infection of a plant by a parasitic nematode, comprising the steps of contacting the nematode with a dsRNA molecule comprising one strand that is substantially identical to a portion of a target gene essential to the nematode, thereby controlling the infection of the plant by the nematode, wherein the target gene is a parasitic nematode pas-5 gene.

The invention further encompasses a method of making a transgenic plant capable of expressing a dsRNA that is substantially identical to a target gene in a parasitic nematode, said method comprising the steps of: (a) preparing a nucleic acid sequence comprising a region that is substantially identical to a portion of a parasitic nematode pas-5 target gene, wherein the nucleic acid is able to form a double-stranded transcript once expressed in the plant; (b) contacting a recipient plant with said nucleic acid; (c) producing one or more offspring of said recipient plant; and (d) testing the offspring for expression of said double-stranded transcript.

In preferred embodiments of the foregoing, the double stranded RNA molecule comprises one strand substantially identical to from about 21 to about 400 or 500 consecutive nucleotides of a sequence selected from the group consisting of: (a) a polynucleotide having a sequence as set forth in SEQ ID NO:1; and (b) a polynucleotide from a parasitic nematode that hybridizes under stringent conditions to a polynucleotide having a sequence as set forth in SEQ ID NO:1.

BRIEF DESCRIPTION OF THE DRAWINGS

FIG. 1 shows the full-length cDNA sequence of *H. glycines* pas-5 gene, which is identified as SEQ ID NO:1.

FIG. 2 provides the sets of primers (SEQ ID NOs:2-13) that were used to isolate the *H. glycines* pas-5 gene and *C. elegans* homologs of the *H. glycines* pas-5 gene (SEQ ID NOs:14-15) by PCR.

FIG. 3 shows the sequences of the *C. elegans* pas-5 gene fragment (SEQ ID NO:16) used in the RNAi feeding assay of Example 3.

DETAILED DESCRIPTION OF THE INVENTION

Figure 4:
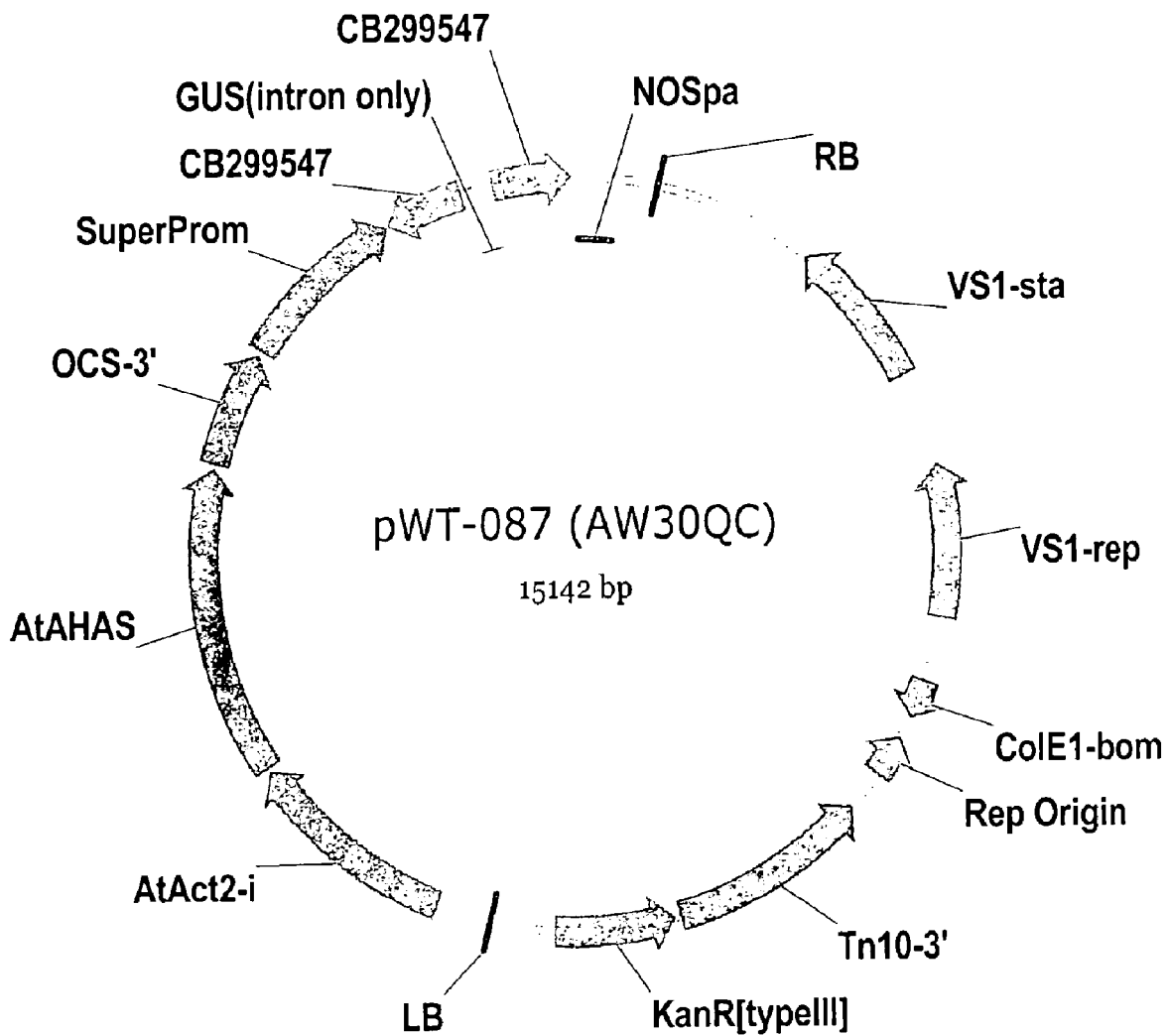
FIG. 4 shows a binary vector useful for transformation of soybean cells to produce the dsRNA of the invention in soybean plants, thereby inhibiting the *H. glycines* pas-5 target genes identified herein.

The present invention may be understood more readily by reference to the following detailed description of the preferred embodiments of the invention and the examples included herein. Unless otherwise noted, the terms used herein are to be understood according to conventional usage by those of ordinary skill in the relevant art. In addition to the definitions of terms provided below, definitions of common terms in molecular biology may also be found in Rieger et al., 1991 Glossary of genetics: classical and molecular, 5$^{th}$ Ed., Berlin: Springer-Verlag; and in Current Protocols in Molecular Biology, F. M. Ausubel et al., Eds., Current Protocols, a joint venture between Greene Publishing Associates, Inc. and John Wiley & Sons, Inc., (1998 Supplement). It is to be understood that as used in the specification and in the claims, "a" or "an" can mean one or more, depending upon the context in which it is used. Thus, for example, reference to "a cell" can mean that at least one cell can be utilized. It is to be understood that this invention is not limited to specific nucleic acids, specific cell types, specific host cells, specific conditions, or specific methods, etc., as such may, of course, vary, and the numerous modifications and variations therein will be apparent to those skilled in the art. It is also to be understood that the terminology used herein is for the purpose of describing specific embodiments only and is not intended to be limiting.

Throughout this application, various publications are referenced. The disclosures of all of these publications and those references cited within those publications in their entireties are hereby incorporated by reference into this application in order to more fully describe the state of the art to which this invention pertains. Standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described in Sambrook et al., 1989 Molecular Cloning, Second Edition, Cold Spring Harbor Laboratory, Plainview, N.Y.; Maniatis et al., 1982 Molecular Cloning, Cold Spring Harbor Laboratory, Plainview, N.Y.; Wu (Ed.) 1993 Meth. Enzymol. 218, Part I; Wu (Ed.) 1979 Meth Enzymol. 68; Wu et al., (Eds.) 1983 Meth. Enzymol. 100 and 101; Grossman and Moldave (Eds.) 1980 Meth. Enzymol. 65; Miller (Ed.) 1972 Experiments in Molecular Genetics, Cold Spring Harbor Laboratory, Cold Spring Harbor, N.Y.; Old and Primrose, 1981 Principles of Gene Manipulation, University of California Press, Berkeley; Schleif and Wensink, 1982 Practical Methods in Molecular Biology; Glover (Ed.) 1985 DNA Cloning Vol. I and II, IRL Press, Oxford, UK; Hames and Higgins (Eds.) 1985 Nucleic Acid Hybridization, IRL Press, Oxford, UK; and Setlow and Hollaender 1979 Genetic Engineering: Principles and Methods, Vols. 1-4, Plenum Press, New York. Abbreviations and nomenclature, where employed, are deemed standard in the field and commonly used in professional journals such as those cited herein.

As used herein, "RNAi" or "RNA interference" refers to the process of sequence-specific post-transcriptional gene silencing in nematodes, mediated by double-stranded RNA (dsRNA). As used herein, "dsRNA" refers to RNA that is partially or completely double stranded. Double stranded RNA is also referred to as short interfering RNA (siRNA), short interfering nucleic acid (siNA), micro-RNA (mRNA), and the like. In the RNAi process, dsRNA comprising a first strand that is substantially identical to a portion of a target gene and a second strand that is complementary to the first strand is introduced into a nematode, preferably by soaking and more preferably by feeding. After introduction into the nematode, the target gene-specific dsRNA is processed into relatively small fragments (siRNAs) and can subsequently become distributed throughout the nematode, leading to a loss-of-function mutation having a phenotype that, over the period of a generation, may come to closely resemble the phenotype arising from a complete or partial deletion of the target gene. Alternatively, the target gene-specific dsRNA is processed into relatively small fragments by a plant cell containing the RNAi processing machinery; and when the plant-processed small dsRNA is ingested by a parasitic nematode, the loss-of-function phenotype is obtained.

As used herein, taking into consideration the substitution of uracil for thymine when comparing RNA and DNA sequences, the terms "substantially identical" and "corresponding to" mean that the nucleotide sequence of one strand of the dsRNA is at least about 80%-90% identical to 20 or more contiguous nucleotides of the target gene, more preferably, at least about 90-95% identical to 20 or more contiguous nucleotides of the target gene, and most preferably at least about 95-99% identical or absolutely identical to 20 or more contiguous nucleotides of the target gene.

As used herein, "complementary" polynucleotides are those that are capable of base pairing according to the standard Watson-Crick complementarity rules. Specifically, purines will base pair with pyrimidines to form a combination of guanine paired with cytosine (G:C) and adenine paired with either thymine (A:T) in the case of DNA, or adenine paired with uracil (A:U) in the case of RNA. It is understood that two polynucleotides may hybridize to each other even if they are not completely complementary to each other, provided that each has at least one region that is substantially complementary to the other. As used herein, the term "substantially complementary" means that two nucleic acid sequences are complementary at least at 80% of their nucleotides. Preferably, the two nucleic acid sequences are complementary at least at 85%, 90%, 95%, 96%, 97%, 98%, 99% or more of their nucleotides. Alternatively, "substantially complementary" means that two nucleic acid sequences can hybridize under high stringency conditions. As used herein, the term "substantially identical" or "corresponding to" means that two nucleic acid sequences have at least 80% sequence identity. Preferably, the two nucleic acid sequences have at least 85%, 90%, 95%, 96%, 97%, 98%, 99% or 100% of sequence identity.

Also as used herein, the terms "nucleic acid" and "polynucleotide" refer to RNA or DNA that is linear or branched, single or double stranded, or a hybrid thereof. The term also encompasses RNA/DNA hybrids. When dsRNA is produced synthetically, less common bases, such as inosine, 5-methylcytosine, 6-methyladenine, hypoxanthine and others can also be used for antisense, dsRNA, and ribozyme pairing. For example, polynucleotides that contain C-5 propyne analogues of uridine and cytidine have been shown to bind RNA with high affinity and to be potent antisense inhibitors of gene expression. Other modifications, such as modification to the phosphodiester backbone, or the 2'-hydroxy in the ribose sugar group of the RNA can also be made.

As used herein, the terms "contacting" and "administering" are used interchangeably, and refer to a process by which dsRNA of the present invention is delivered to a cell of a parasitic nematode, in order to inhibit expression of an essential target gene in the nematode. The dsRNA may be administered in a number of ways, including, but not limited to, direct introduction into a cell (i.e., intracellularly); or extracellular introduction into a cavity, interstitial space, or into the circulation of the nematode, oral introduction, the dsRNA may be introduced by bathing the nematode in a solution containing dsRNA, or the dsRNA may be present in food source. Methods for oral introduction include direct mixing of dsRNA with food of the nematode, as well as engineered approaches in which a species that is used as food is engineered to express a dsRNA, then fed to the organism to be affected. For example, the dsRNA may be sprayed onto a plant, or the dsRNA may be applied to soil in the vicinity of roots, taken up by the plant and/or the parasitic nematode, or a plant may be genetically engineered to express the dsRNA in an amount sufficient to kill some or all of the parasitic nematode to which the plant is exposed.

As used herein, the term "control", when used in the context of an infection, refers to the reduction or prevention of an infection. Reducing or preventing an infection by a nematode will cause a plant to have increased resistance to the nematode, however, such increased resistance does not imply that the plant necessarily has 100% resistance to infection. In preferred embodiments, the resistance to infection by a nematode in a resistant plant is greater than 10%, 20%, 30%, 40%, 50%, 60%, 70%, 80%, 90%, or 95% in comparison to a wild type plant that is not resistant to nematodes. The plant's resistance to infection by the nematode may be due to the death, sterility, arrest in development, or impaired mobility of the nematode upon exposure to the dsRNA specific to an essential gene.

The term "plant" is intended to encompass plants at any stage of maturity or development, as well as any tissues or organs (plant parts) taken or derived from any such plant unless otherwise clearly indicated by context. Plant parts include, but are not limited to, stems, roots, flowers, ovules, stamens, leaves, embryos, meristematic regions, callus tissue, anther cultures, gametophytes, sporophytes, pollen, microspores, protoplasts, hairy root cultures, and the like. The present invention also includes seeds produced by the plants of the present invention. In one embodiment, the seeds are true breeding for an increased resistance to nematode infection as compared to a wild-type variety of the plant seed. In a preferred embodiment of the invention, the plant is a soybean plant. As used herein, a "plant cell" includes, but is not limited to, a protoplast, gamete producing cell, and a cell that regenerates into a whole plant. Tissue culture of various tissues of plants and regeneration of plants therefrom is well known in the art and is widely published.

As used herein, the term "transgenic" refers to any plant, plant cell, callus, plant tissue, or plant part that contains all or part of at least one recombinant polynucleotide. In many cases, all or part of the recombinant polynucleotide is stably integrated into a chromosome or stable extra-chromosomal element, so that it is passed on to successive generations. For the purposes of the invention, the term "recombinant polynucleotide" refers to a polynucleotide that has been altered, rearranged, or modified by genetic engineering. Examples include any cloned polynucleotide, or polynucleotides, that are linked or joined to heterologous sequences. The term "recombinant" does not refer to alterations of polynucleotides that result from naturally occurring events, such as spontaneous mutations, or from non-spontaneous mutagenesis followed by selective breeding.

As used herein, the term "amount sufficient to inhibit expression" refers to a concentration or amount of the dsRNA that is sufficient to reduce levels or stability of mRNA or protein produced from a target gene in a parasitic nematode. As used herein, "inhibiting expression" refers to the absence or observable decrease in the level of protein and/or mRNA product from a target gene. Inhibition of target gene expression may be lethal to the parasitic nematode, or such inhibition may delay or prevent entry into a particular developmental step (e.g., metamorphosis), if plant disease is associated with a particular stage of the parasitic nematode's life cycle. The consequences of inhibition can be confirmed by examination of the outward properties of the nematode (as presented below in the examples).

The present invention may be used to reduce crop destruction by a variety of plant parasitic nematodes. Some such plants and their pathogens are listed in Index of Plant Diseases in the United States (U.S. Dept. of Agriculture Handbook No. 165, 1960); Distribution of Plant-Parasitic Nematode Species in North America (Society of Nematologists, 1985); and Fungi on Plants and Plant Products in the United States (American Phytopathological Society, 1989). In a preferred embodiment, the present invention uses RNAi to reduce crop destruction by parasitic nematodes, and most particularly, by cyst nematodes, for example, *Heterodera glycines, Heterodera shachtii, Heterodera avenae, Heterodera oryzae, Globodera pallida, Globodera rostochiensis*, or *Globodera tabacum*.

In accordance with the invention, a parasitic nematode is contacted with a dsRNA, which specifically inhibits expression of a target gene, which is essential for survival, metamorphosis, or reproduction of the nematode. Preferably, the parasitic nematode comes into contact with the dsRNA after entering a plant, which expresses the dsRNA. In one embodiment, the dsRNA is encoded by a vector, which has been transformed into an ancestor of the infected plant. Preferably, the nucleic acid sequence expressing said dsRNA is under the transcriptional control of a root specific promoter or a parasitic nematode feeding cell-specific promoter.

In one embodiment, the parasitic nematode target gene is a homolog of the *C. elegans* pas-5 gene, which encodes a member of the proteasome α subunit gene class. pas-5 has endopeptidase activity required for embryonic and larval development, reproduction, and proper locomotory behavior in *C. elegans*. Example 2 below shows that feeding *C. elegans* RNAi molecules specific for the pas-5 gene results in lethality at the early larval stage. In this embodiment of the present invention, the parasitic nematode pas -5 target gene comprises a sequence selected from the group consisting of: (a) the sequence set forth in SEQ ID NO:1 and (b) a polynucleotide from a parasitic nematode that hybridizes under stringent conditions to the sequence set forth in SEQ ID NO:1.

Complete cDNAs corresponding to the pas-5 target gene of the invention may be isolated from parasitic nematodes other than *H. glycines* using the information provided herein and techniques known to those of skill in the art of biotechnology. For example, a nucleic acid molecule from a parasitic nematode that hybridizes under stringent conditions to a nucleotide sequence of SEQ ID NO:1 can be isolated from parasitic nematode cDNA libraries. Alternatively, mRNA can be isolated from parasitic nematode cells (e.g., by the guanidinium-thiocyanate extraction procedure of Chirgwin et al., 1979, Biochemistry 18:5294-5299), and cDNA can be prepared using reverse transcriptase (e.g., Moloney MLV reverse transcriptase, available from Gibco/BRL, Bethesda, Md.; or AMV reverse transcriptase, available from Seikagaku America, Inc., St. Petersburg, Fla.). Synthetic oligonucleotide primers for polymerase chain reaction amplification can be designed based upon the nucleotide sequence shown in SEQ ID NO:1. Nucleic acid molecules corresponding to the parasitic nematode target genes of the invention can be amplified using cDNA or, alternatively, genomic DNA, as a template and appropriate oligonucleotide primers according to standard PCR amplification techniques. The nucleic acid molecules so amplified can be cloned into appropriate vectors and characterized by DNA sequence analysis. The nucleic acid sequences determined from the cloning of the genes from soybean cyst nematode allow for the generation of probes and primers designed for use in identifying and/or cloning homologs in other cell types and organisms, as well as homologs from other nematodes and related species.

Accordingly, the dsRNA of the invention is substantially identical to a portion of the pas-5 target gene of a parasitic nematode genome. In preferred embodiments, the target gene is selected from the group consisting of: (a) a polynucleotide having the sequence set forth in SEQ ID NO:1; and (b) a polynucleotide from a parasitic nematode that hybridizes under stringent conditions to a polynucleotide having the sequence set forth in SEQ ID NO:1. Preferably, the dsRNA of the invention comprises (a) a first strand comprising a sequence that is substantially identical to from about 21 to about 400 or 500 consecutive nucleotides of the target gene and (b) a second strand comprising a sequence substantially complementary to the first strand.

As discussed above, fragments of dsRNA larger than about 21 nucleotides in length are cleaved intracellularly by nematodes and plants to siRNAs of about 21 nucleotides in length, and these siRNAs are the actual mediators of the RNAi phenomenon. Example 5 demonstrates that siRNAs are generated when a vector containing the *H. glycines* pas-5 target gene is transformed into soybean hairy roots. Example 4 demonstrates that cyst count is reduced when *H. glycines* is inoculated onto transgenic soybean hairy roots containing the *H. glycines* pas-5 target gene, as compared to a *H. glycines*-inoculated transgenic control hairy root line that does not contain the *H. glycines* pas-5 target gene. Thus the dsRNA of the present invention may range in length from about 21 nucleotides to about 978 nucleotides. Preferably, the dsRNA of the invention has a length from about 21 nucleotides to about 900 nucleotides. More preferably, the dsRNA of the invention has a length from about 21 nucleotides to about 750 nucleotides, or from about 21 nucleotides to about 400 or 500 nucleotides.

When dsRNA of the invention has a length longer than about 21 nucleotides, for example from about 50 nucleotides to about 978 nucleotides, it will be cleaved randomly to dsRNAs of about 21 nucleotides within the plant or parasitic nematode cell, the siRNAs. The cleavage of a longer dsRNA of the invention will yield a pool of 21 mer dsRNAs, derived from the longer dsRNA. This pool of 21 mer dsRNAs is also encompassed within the scope of the present invention, whether generated intracellularly within the plant or nematode or synthetically using known methods of oligonucleotide synthesis.

The siRNAs of the invention have sequences corresponding to fragments of about 21 contiguous nucleotides across the entire sequence of the *H. glycines* pas-5 target gene. For example, a pool of siRNA of the invention derived from the *H. glycines* pas-5 gene as set forth in SEQ ID NO:1 may comprise a multiplicity of RNA molecules which are selected from the group consisting of oligonucleotides substantially identical to nucleotides 1 to 21 of SEQ ID NO:1, nucleotides 2 to 23 of SEQ ID NO:1, nucleotides 3 to 24 of SEQ ID NO:1, nucleotides 4 to 25 of SEQ ID NO:1, nucleotides 5 to 26 of SEQ ID NO:1, nucleotides 6 to 27 of SEQ ID NO:1, nucleotides 7 to 28 of SEQ ID NO:1, nucleotides 8 to 29 of SEQ ID NO:1, nucleotides 9 to 30 of SEQ ID NO:1, nucleotides 10 to 31 of SEQ ID NO:1, nucleotides 11 to 32 of SEQ ID NO:1, nucleotides 12 to 33 of SEQ ID NO:1, nucleotides 13 to 34 of SEQ ID NO:1, nucleotides 14 to 35 of SEQ ID NO:1, nucleotides 15 to 36 of SEQ ID NO:1, nucleotides 16 to 37 of SEQ ID NO:1, nucleotides 17 to 38 of SEQ ID NO:1, nucleotides 18 to 39 of SEQ ID NO:1, nucleotides 19 to 40 of SEQ ID NO:1, nucleotides 20 to 41 of SEQ ID NO:1, nucleotides 21 to 42 of SEQ ID NO:1, nucleotides 22 to 43 of SEQ ID NO:1, nucleotides 23 to 44 of SEQ ID NO:1, nucleotides 24 to 45 of SEQ ID NO:1, nucleotides 25 to 46 of SEQ ID NO:1, nucleotides 26 to 47 of SEQ ID NO:1, nucleotides 27 to 48 of SEQ ID NO:1, nucleotides 28 to 49 of SEQ ID NO:1, nucleotides 29 to 50 of SEQ ID NO:1, nucleotides 30 to 51 of SEQ ID NO:1, nucleotides 31 to 52 of SEQ ID NO:1, nucleotides 32 to 53 of SEQ ID NO:1, nucleotides 33 to 54 of SEQ ID NO:1, nucleotides 34 to 55 of SEQ ID NO:1, nucleotides 35 to 56 of SEQ ID NO:1, nucleotides 36 to 57 of SEQ ID NO:1, nucleotides 37 to 58 of SEQ ID NO:1, nucleotides 38 to 59 of SEQ ID NO:1, nucleotides 39 to 60 of SEQ ID NO:1, nucleotides 40 to 61 of SEQ ID NO:1, nucleotides 41 to 62 of SEQ ID NO:1, nucleotides 42 to 63 of SEQ ID NO:1, nucleotides 43 to 64 of SEQ ID NO:1, nucleotides 44 to 65 of SEQ ID NO:1, nucleotides 45 to 66 of SEQ ID NO:1, nucleotides 46 to 67 of SEQ ID NO:1, nucleotides 47 to 68 of SEQ ID NO:1, nucleotides 48 to 69 of SEQ ID NO:1, nucleotides 49 to 70 of SEQ ID NO:1, and nucleotides 50 to 71 of SEQ ID NO:1.

As another example, a pool of siRNA of the invention derived from the *H. glycines* pas-5 gene, as set forth in SEQ ID NO:1, may comprise a multiplicity of RNA molecules substantially identical to nucleotides 51 to 72 of SEQ ID NO:1, nucleotides 52 to 73 of SEQ ID NO:1, nucleotides 53 to 74 of SEQ ID NO:1, nucleotides 54 to 75 of SEQ ID NO:1, nucleotides 55 to 76 of SEQ ID NO:1, nucleotides 56 to 77 of SEQ ID NO:1, nucleotides 57 to 78 of SEQ ID NO:1, nucleotides 58 to 79 of SEQ ID NO:1, nucleotides 59 to 80 of SEQ ID NO:1, nucleotides 60 to 81 of SEQ ID NO:1, nucleotides 61 to 82 of SEQ ID NO:1, nucleotides 62 to 83 of SEQ ID NO:1, nucleotides 63 to 84 of SEQ ID NO:1, nucleotides 64 to 85 of SEQ ID NO:1, nucleotides 65 to 86 of SEQ ID NO:1, nucleotides 66 to 87 of SEQ ID NO:1, nucleotides 67 to 88 of SEQ ID NO:1, nucleotides 68 to 89 of SEQ ID NO:1, nucleotides 69 to 90 of SEQ ID NO:1, nucleotides 70 to 91 of SEQ ID NO:1, nucleotides 71 to 92 of SEQ ID NO:1, nucleotides 72 to 93 of SEQ ID NO:1, nucleotides 73 to 94 of SEQ ID NO:1, nucleotides 74 to 95 of SEQ ID NO:1, nucleotides 75 to 96 of SEQ ID NO:1, nucleotides 76 to 97 of SEQ ID NO:1, nucleotides 77 to 98 of SEQ ID NO:1, nucleotides 78 to 99 of SEQ ID NO:1, nucleotides 79 to 100 of SEQ ID NO:1, nucleotides 80 to 101 of SEQ ID NO:1, nucleotides 81 to 102 of SEQ ID NO:1, nucleotides 82 to 103 of SEQ ID NO:1, nucleotides 83 to 104 of SEQ ID NO:1, nucleotides 84 to 105 of SEQ ID NO:1, nucleotides 85 to 106 of SEQ ID NO:1, nucleotides 86 to 107 of SEQ ID NO:1, nucleotides 87 to 108 of SEQ ID NO:1, nucleotides 88 to 109 of SEQ ID NO:1, nucleotides 89 to 110 of SEQ ID NO:1, nucleotides 90 to 111 of SEQ ID NO:1, nucleotides 91 to 112 of SEQ ID NO:1, nucleotides 92 to 113 of SEQ ID NO:1, nucleotides 93 to 114 of SEQ ID NO:1, nucleotides 94 to 115 of SEQ ID NO:1, nucleotides 95 to 116 of SEQ ID NO:1, nucleotides 96 to 117 of SEQ ID NO:1, nucleotides 97 to 118 of SEQ ID NO:1, nucleotides 98 to 119 of SEQ ID NO:1, nucleotides 99 to 120 of SEQ ID NO:1, and nucleotides 100 to 121 of SEQ ID NO:1.

As another example, a pool of siRNA of the invention derived from the *H. glycines* pas-5 gene, as set forth in SEQ ID NO:1, may comprise a multiplicity of RNA molecules substantially identical to nucleotides 101 to 122 of SEQ ID NO:1, nucleotides 102 to 123 of SEQ ID NO:1, nucleotides 103 to 124 of SEQ ID NO:1, nucleotides 104 to 125 of SEQ ID NO:1, nucleotides 105 to 126 of SEQ ID NO:1, nucleotides 106 to 127 of SEQ ID NO:1, nucleotides 107 to 128 of SEQ ID NO:1, nucleotides 108 to 129 of SEQ ID NO:1, nucleotides 109 to 130 of SEQ ID NO:1, nucleotides 110 to 131 of SEQ ID NO:1, nucleotides 111 to 132 of SEQ ID NO:1, nucleotides 112 to 133 of SEQ ID NO:1, nucleotides 113 to 134 of SEQ ID NO:1, nucleotides 114 to 135 of SEQ ID NO:1, nucleotides 15 to 136 of SEQ ID NO:1, nucleotides 116 to 137 of SEQ ID NO:1, nucleotides 117 to 138 of SEQ ID NO:1, nucleotides 118 to 139 of SEQ ID NO:1, nucleotides 119 to 140 of SEQ ID NO:1, nucleotides 120 to 141 of SEQ ID NO:1, nucleotides 121 to 142 of SEQ ID NO:1, nucleotides 122 to 143 of SEQ ID NO:1, nucleotides 123 to 144 of SEQ ID NO:1, nucleotides 124 to 145 of SEQ ID NO:1, nucleotides 125 to 146 of SEQ ID NO:1, nucleotides 126 to 147 of SEQ ID NO:1, nucleotides 127 to 148 of SEQ ID NO:1, nucleotides 128 to 149 of SEQ ID NO:1, nucleotides 129 to 150 of SEQ ID NO:1, nucleotides 130 to 151 of SEQ ID NO:1, nucleotides 131 to 152 of SEQ ID NO:1, nucleotides 132 to 153 of SEQ ID NO:1, nucleotides 133 to 154 of SEQ ID NO:1, nucleotides 134 to 155 of SEQ ID NO:1, nucleotides 135 to 156 of SEQ ID NO:1, nucleotides 136 to 157 of SEQ ID NO:1, nucleotides 137 to 158 of SEQ ID NO:1, nucleotides 138 to 159 of SEQ ID NO:1, nucleotides 139 to 160 of SEQ ID NO:1, nucleotides 140 to 161 of SEQ ID NO:1, nucleotides 141 to 162 of SEQ ID NO:1, nucleotides 142 to 163 of SEQ ID NO:1, nucleotides 143 to 164 of SEQ ID NO:1, nucleotides 144 to 165 of SEQ ID NO:1, nucleotides 145 to 166 of SEQ ID NO:1, nucleotides 146 to 167 of SEQ ID NO:1, nucleotides 147 to 168 of SEQ ID NO:1, nucleotides 148 to 169 of SEQ ID NO:1, nucleotides 149 to 170 of SEQ ID NO:1, and nucleotides 150 to 171 of SEQ ID NO:1.

As another example, a pool of siRNA of the invention derived from the *H. glycines* pas-5 gene, as set forth in SEQ ID NO:1, may comprise a multiplicity of RNA molecules substantially identical to nucleotides 151 to 172 of SEQ ID NO:1, nucleotides 152 to 173 of SEQ ID NO:1, nucleotides 153 to 174 of SEQ ID NO:1, nucleotides 154 to 175 of SEQ ID NO:1, nucleotides 155 to 176 of SEQ ID NO:1, nucleotides 156 to 177 of SEQ ID NO:1, nucleotides 157 to 178 of SEQ ID NO:1, nucleotides 158 to 179 of SEQ ID NO:1, nucleotides 159 to 180 of SEQ ID NO:1, nucleotides 160 to 181 of SEQ ID NO:1, nucleotides 161 to 182 of SEQ ID NO:1, nucleotides 162 to 183 of SEQ ID NO:1, nucleotides 163 to 184 of SEQ ID NO:1, nucleotides 164 to 185 of SEQ ID NO:1, nucleotides 165 to 186 of SEQ ID NO:1, nucleotides 166 to 187 of SEQ ID NO:1, nucleotides 167 to 188 of SEQ ID NO:1, nucleotides 168 to 189 of SEQ ID NO:1, nucleotides 169 to 190 of SEQ ID NO:1, nucleotides 170 to 191 of SEQ ID NO:1, nucleotides 171 to 192 of SEQ ID NO:1, nucleotides 172 to 193 of SEQ ID NO:1, nucleotides 173 to 194 of SEQ ID NO:1, nucleotides 174 to 195 of SEQ ID NO:1, nucleotides 175 to 196 of SEQ ID NO:1, nucleotides 176 to 197 of SEQ ID NO:1, nucleotides 177 to 198 of SEQ ID NO:1, nucleotides 178 to 199 of SEQ ID NO:1, nucleotides 179 to 200 of SEQ ID NO:1, nucleotides 180 to 201 of SEQ ID NO:1, nucleotides 181 to 202 of SEQ ID NO:1, nucleotides 182 to 203 of SEQ ID NO:1, nucleotides 183 to 204 of SEQ ID NO:1, nucleotides 184 to 205 of SEQ ID NO:1, nucleotides 185 to 206 of SEQ ID NO:1, nucleotides 186 to 207 of SEQ ID NO:1, nucleotides 187 to 208 of SEQ ID NO:1, nucleotides 188 to 209 of SEQ ID NO:1, nucleotides 189 to 210 of SEQ ID NO:1, nucleotides 190 to 211 of SEQ ID NO:1, nucleotides 191 to 212 of SEQ ID NO:1, nucleotides 192 to 213 of SEQ ID NO:1, nucleotides 193 to 214 of SEQ ID NO:1, nucleotides 194 to 215 of SEQ ID NO:1, nucleotides 195 to 216 of SEQ ID NO:1, nucleotides 196 to 217 of SEQ ID NO:1, nucleotides 197 to 218 of SEQ ID NO:1, nucleotides 198 to 219 of SEQ ID NO:1, nucleotides 199 to 220 of SEQ ID NO:1, and nucleotides 200 to 221 of SEQ ID NO:1.

As another example, a pool of siRNA of the invention derived from the *H. glycines* pas-5 gene, as set forth in SEQ ID NO:1, may comprise a multiplicity of RNA molecules substantially identical to nucleotides 201 to 222 of SEQ ID NO:1, nucleotides 202 to 223 of SEQ ID NO:1, nucleotides 203 to 224 of SEQ ID NO:1, nucleotides 204 to 225 of SEQ ID NO:1, nucleotides 205 to 226 of SEQ ID NO:1, nucleotides 206 to 227 of SEQ ID NO:1, nucleotides 207 to 228 of SEQ ID NO:1, nucleotides 208 to 229 of SEQ ID NO:1, nucleotides 209 to 230 of SEQ ID NO:1, nucleotides 210 to 231 of SEQ ID NO:1, nucleotides 211 to 232 of SEQ ID NO:1, nucleotides 212 to 233 of SEQ ID NO:1, nucleotides 213 to 234 of SEQ ID NO:1, nucleotides 214 to 235 of SEQ ID NO:1, nucleotides 215 to 236 of SEQ ID NO:1, nucleotides 216 to 237 of SEQ ID NO:1, nucleotides 217 to 238 of SEQ ID NO:1, nucleotides 218 to 239 of SEQ ID NO:1, nucleotides 219 to 240 of SEQ ID NO:1, nucleotides 220 to 241 of SEQ ID NO:1, nucleotides 221 to 242 of SEQ ID NO:1, nucleotides 222 to 243 of SEQ ID NO:1, nucleotides 223 to 244 of SEQ ID NO:1, nucleotides 224 to 245 of SEQ ID NO:1, nucleotides 225 to 246 of SEQ ID NO:1, nucleotides 226 to 247 of SEQ ID NO:1, nucleotides 227 to 248 of SEQ ID NO:1, nucleotides 228 to 249 of SEQ ID NO:1, nucleotides 229 to 250 of SEQ ID NO:1, nucleotides 230 to 251 of SEQ ID NO:1, nucleotides 231 to 252 of SEQ ID NO:1, nucleotides 232 to 253 of SEQ ID NO:1, nucleotides 233 to 254 of SEQ ID NO:1, nucleotides 234 to 255 of SEQ ID NO:1, nucleotides 235 to 256 of SEQ ID NO:1, nucleotides 236 to 257 of SEQ ID NO:1, nucleotides 237 to 258 of SEQ ID NO:1, nucleotides 238 to 259 of SEQ ID NO:1, nucleotides 239 to 260 of SEQ ID NO:1, nucleotides 240 to 261 of SEQ ID NO:1, nucleotides 241 to 262 of SEQ ID NO:1, nucleotides 242 to 263 of SEQ ID NO:1, nucleotides 243 to 264 of SEQ ID NO:1, nucleotides 244 to 265 of SEQ ID NO:1, nucleotides 245 to 266 of SEQ ID NO:1, nucleotides 246 to 267 of SEQ ID NO:1, nucleotides 247 to 268 of SEQ ID NO:1, nucleotides 248 to 269 of SEQ ID NO:1, nucleotides 249 to 270 of SEQ ID NO:1, and nucleotides 250 to 271 of SEQ ID NO:1.

As another example, a pool of siRNA of the invention derived from the *H. glycines* pas-5 gene, as set forth in SEQ ID NO:1, may comprise a multiplicity of RNA molecules substantially identical to nucleotides 251 to 272 of SEQ ID NO:1, nucleotides 252 to 273 of SEQ ID NO:1, nucleotides 253 to 274 of SEQ ID NO:1, nucleotides 254 to 275 of SEQ ID NO:1, nucleotides 255 to 276 of SEQ ID NO:1, nucleotides 256 to 277 of SEQ ID NO:1, nucleotides 257 to 278 of SEQ ID NO:1, nucleotides 258 to 279 of SEQ ID NO:1, nucleotides 259 to 280 of SEQ ID NO:1, nucleotides 260 to 281 of SEQ ID NO:1, nucleotides 261 to 282 of SEQ ID NO:1, nucleotides 262 to 283 of SEQ ID NO:1, nucleotides 263 to 284 of SEQ ID NO:1, nucleotides 264 to 285 of SEQ ID NO:1, nucleotides 265 to 286 of SEQ ID NO:1, nucleotides 266 to 287 of SEQ ID NO:1, nucleotides 267 to 288 of SEQ ID NO:1, nucleotides 268 to 289 of SEQ ID NO:1, nucleotides 269 to 290 of SEQ ID NO:1, nucleotides 270 to 291 of SEQ ID NO:1, nucleotides 271 to 292 of SEQ ID NO:1, nucleotides 272 to 293 of SEQ ID NO:1, nucleotides 273 to 294 of SEQ ID NO:1, nucleotides 274 to 295 of SEQ ID NO:1, nucleotides 275 to 296 of SEQ ID NO:1, nucleotides 276 to 297 of SEQ ID NO:1, nucleotides 277 to 298 of SEQ ID NO:1, nucleotides 278 to 299 of SEQ ID NO:1, nucleotides 279 to 300 of SEQ ID NO:1, nucleotides 280 to 301 of SEQ ID NO:1, nucleotides 281 to 302 of SEQ ID NO:1, nucleotides 282 to 303 of SEQ ID NO:1, nucleotides 283 to 304 of SEQ ID NO:1, nucleotides 284 to 305 of SEQ ID NO:1, nucleotides 285 to 306 of SEQ ID NO:1, nucleotides 286 to 307 of SEQ ID NO:1, nucleotides 287 to 308 of SEQ ID NO:1, nucleotides 288 to 309 of SEQ ID NO:1, nucleotides 289 to 310 of SEQ ID NO:1, nucleotides 290 to 311 of SEQ ID NO:1, nucleotides 291 to 312 of SEQ ID NO:1, nucleotides 292 to 313 of SEQ ID NO:1, nucleotides 293 to 314 of SEQ ID NO:1, nucleotides 294 to 315 of SEQ ID NO:1, nucleotides 295 to 316 of SEQ ID NO:1, nucleotides 296 to 317 of SEQ ID NO:1, nucleotides 297 to 318 of SEQ ID NO:1, nucleotides 298 to 319 of SEQ ID NO:1, nucleotides 299 to 320 of SEQ ID NO:1, and nucleotides 300 to 321 of SEQ ID NO:1.

As another example, a pool of siRNA of the invention derived from the *H. glycines* pas-5 gene, as set forth in SEQ ID NO:1, may comprise a multiplicity of RNA molecules substantially identical to nucleotides 301 to 322 of SEQ ID NO:1, nucleotides 302 to 323 of SEQ ID NO:1, nucleotides 303 to 324 of SEQ ID NO:1, nucleotides 304 to 325 of SEQ ID NO:1, nucleotides 305 to 326 of SEQ ID NO:1, nucleotides 306 to 327 of SEQ ID NO:1, nucleotides 307 to 328 of SEQ ID NO:1, nucleotides 308 to 329 of SEQ ID NO:1, nucleotides 309 to 330 of SEQ ID NO:1, nucleotides 310 to 331 of SEQ ID NO:1, nucleotides 311 to 332 of SEQ ID NO:1, nucleotides 312 to 333 of SEQ ID NO:1, nucleotides 313 to 334 of SEQ ID NO:1, nucleotides 314 to 335 of SEQ ID NO:1, nucleotides 315 to 336 of SEQ ID NO:1, nucleotides 316 to 337 of SEQ ID NO:1, nucleotides 317 to 338 of SEQ ID NO:1, nucleotides 318 to 339 of SEQ ID NO:1, nucleotides 319 to 340 of SEQ ID NO:1, nucleotides 320 to 341 of SEQ ID NO:1, nucleotides 321 to 342 of SEQ ID NO:1, nucleotides 322 to 343 of SEQ ID NO:1, nucleotides 323 to 344 of SEQ ID NO:1, nucleotides 324 to 345 of SEQ ID NO:1, nucleotides 325 to 346 of SEQ ID NO:1, nucleotides 326 to 347 of SEQ ID NO:1, nucleotides 327 to 348 of SEQ ID NO:1, nucleotides 328 to 349 of SEQ ID NO:1, nucleotides 329 to 350 of SEQ ID NO:1, nucleotides 330 to 351 of SEQ ID NO:1, nucleotides 331 to 352 of SEQ ID NO:1, nucleotides 332 to 353 of SEQ ID NO:1, nucleotides 333 to 354 of SEQ ID NO:1, nucleotides 334 to 355 of SEQ ID NO:1, nucleotides 335 to 356 of SEQ ID NO:1, nucleotides 336 to 357 of SEQ ID NO:1, nucleotides 337 to 358 of SEQ ID NO:1, nucleotides 338 to 359 of SEQ ID NO:1, nucleotides 339 to 360 of SEQ ID NO:1, nucleotides 340 to 361 of SEQ ID NO:1, nucleotides 341 to 362 of SEQ ID NO:1, nucleotides 342 to 363 of SEQ ID NO:1, nucleotides 343 to 364 of SEQ ID NO:1, nucleotides 344 to 365 of SEQ ID NO:1, nucleotides 345 to 366 of SEQ ID NO:1, nucleotides 346 to 367 of SEQ ID NO:1, nucleotides 347 to 368 of SEQ ID NO:1, nucleotides 348 to 369 of SEQ ID NO:1, nucleotides 349 to 370 of SEQ ID NO:1, and nucleotides 350 to 371 of SEQ ID NO:1.

As another example, a pool of siRNA molecules derived from the *H. glycines* pas-5 gene, as set forth in SEQ ID NO:1, may comprise a multiplicity of RNA molecules substantially identical to nucleotides 351 to 372 of SEQ ID NO:1, nucleotides 352 to 373 of SEQ ID NO:1, nucleotides 353 to 374 of SEQ ID NO:1, nucleotides 354 to 375 of SEQ ID NO:1, nucleotides 355 to 376 of SEQ ID NO:1, nucleotides 356 to 377 of SEQ ID NO:1, nucleotides 357 to 378 of SEQ ID NO:1, nucleotides 358 to 379 of SEQ ID NO:1, nucleotides 359 to 380 of SEQ ID NO:1, nucleotides 360 to 381 of SEQ ID NO:1, nucleotides 361 to 382 of SEQ ID NO:1, nucleotides 362 to 383 of SEQ ID NO:1, nucleotides 363 to 384 of SEQ ID NO:1, nucleotides 364 to 385 of SEQ ID NO:1, nucleotides 365 to 386 of SEQ ID NO:1, nucleotides 366 to 387 of SEQ ID NO:1, nucleotides 367 to 388 of SEQ ID NO:1, nucleotides 368 to 389 of SEQ ID NO:1, nucleotides 369 to 390 of SEQ ID NO:1, nucleotides 370 to 391 of SEQ ID NO:1, nucleotides 371 to 392 of SEQ ID NO:1, nucleotides 372 to 393 of SEQ ID NO:1, nucleotides 373 to 394 of SEQ ID NO:1, nucleotides 374 to 395 of SEQ ID NO:1, nucleotides 375 to 396 of SEQ ID NO:1, nucleotides 376 to 397 of SEQ ID NO:1, nucleotides 377 to 398 of SEQ ID NO:1, nucleotides 378 to 399 of SEQ ID NO:1, nucleotides 379 to 400 of SEQ ID NO:1; nucleotides 380 to 401 of SEQ ID NO:1, nucleotides 381 to 402 of SEQ ID NO:1, nucleotides 382 to 403 of SEQ ID NO:1, nucleotides 383 to 404 of SEQ ID NO:1, nucleotides 384 to 405 of SEQ ID NO:1, nucleotides 385 to 406 of SEQ ID NO:1, nucleotides 386 to 407 of SEQ ID NO:1, nucleotides 387 to 408 of SEQ ID NO:1, nucleotides 388 to 409 of SEQ ID NO:1, nucleotides 389 to 410 of SEQ ID NO:1, nucleotides 390 to 411 of SEQ ID NO:1, nucleotides 391 to 412 of SEQ ID NO:1, nucleotides 392 to 413 of SEQ ID NO:1, nucleotides 393 to 414 of SEQ ID NO:1, nucleotides 394 to 415 of SEQ ID NO:1, nucleotides 395 to 416 of SEQ ID NO:1, nucleotides 396 to 417 of SEQ ID NO:1, nucleotides 397 to 418 of SEQ ID NO:1, nucleotides 398 to 419 of SEQ ID NO:1, nucleotides 399 to 420 of SEQ ID NO:1, and nucleotides 400 to 421 of SEQ ID NO:1.

As another example, a pool of siRNA molecules of the invention derived from the *H. glycines* pas-5 gene, as set forth in SEQ ID NO:1, may comprise a multiplicity of RNA molecules substantially identical to nucleotides 401 to 422 of SEQ ID NO:1, nucleotides 402 to 423 of SEQ ID NO:1, nucleotides 403 to 424 of SEQ ID NO:1, nucleotides 404 to 425 of SEQ ID NO:1, nucleotides 405 to 426 of SEQ ID NO:1, nucleotides 406 to 427 of SEQ ID NO:1, nucleotides 407 to 428 of SEQ ID NO:1, nucleotides 408 to 429 of SEQ ID NO:1, nucleotides 409 to 430 of SEQ ID NO:1, nucleotides 410 to 431 of SEQ ID NO:1, nucleotides 411 to 432 of SEQ ID NO:1, nucleotides 412 to 433 of SEQ ID NO:1, nucleotides 413 to 434 of SEQ ID NO:1, nucleotides 414 to 435 of SEQ ID NO:1, nucleotides 415 to 436 of SEQ ID NO:1, nucleotides 416 to 437 of SEQ ID NO:1, nucleotides 417 to 438 of SEQ ID NO:1, nucleotides 418 to 439 of SEQ ID NO:1, nucleotides 419 to 440 of SEQ ID NO:1, nucleotides 420 to 441 of SEQ ID NO:1, nucleotides 421 to 442 of SEQ ID NO:1, nucleotides 422 to 443 of SEQ ID NO:1, nucleotides 423 to 444 of SEQ ID NO:1, nucleotides 424 to 445 of SEQ ID NO:1, nucleotides 425 to 446 of SEQ ID NO:1, nucleotides 426 to 447 of SEQ ID NO:1, nucleotides 427 to 448 of SEQ ID NO:1, nucleotides 428 to 449 of SEQ ID NO:1, nucleotides 429 to 450 of SEQ ID NO:1, nucleotides 430 to 451 of SEQ ID NO:1, nucleotides 431 to 452 of SEQ ID NO:1, nucleotides 432 to 453 of SEQ ID NO:1, nucleotides 433 to 454 of SEQ ID NO:1, nucleotides 434 to 455 of SEQ ID NO:1, nucleotides 435 to 456 of SEQ ID NO:1, nucleotides 436 to 457 of SEQ ID NO:1, nucleotides 437 to 458 of SEQ ID NO:1, nucleotides 438 to 459 of SEQ ID NO:1, nucleotides 439 to 460 of SEQ ID NO:1, nucleotides 440 to 461 of SEQ ID NO:1, nucleotides 441 to 462 of SEQ ID NO:1, nucleotides 442 to 463 of SEQ ID NO:1, nucleotides 443 to 464 of SEQ ID NO:1, nucleotides 444 to 465 of SEQ ID NO:1, nucleotides 445 to 466 of SEQ ID NO:1, nucleotides 446 to 467 of SEQ ID NO:1, nucleotides 447 to 468 of SEQ ID NO:1, nucleotides 448 to 469 of SEQ ID NO:1, nucleotides 449 to 470 of SEQ ID NO:1, and nucleotides 450 to 471 of SEQ ID NO:1.

As another example, a pool of siRNA molecules of the invention derived from the *H. glycines* pas-5 gene, as set forth in SEQ ID NO:1, may comprise a multiplicity of RNA molecules substantially identical to nucleotides 451 to 472 of SEQ ID NO:1, nucleotides 452 to 473 of SEQ ID NO:1, nucleotides 453 to 474 of SEQ ID NO:1, nucleotides 454 to 475 of SEQ ID NO:1, nucleotides 455 to 476 of SEQ ID NO:1, nucleotides 456 to 477 of SEQ ID NO:1, nucleotides 457 to 478 of SEQ ID NO:1, nucleotides 458 to 479 of SEQ ID NO:1, nucleotides 459 to 480 of SEQ ID NO:1, nucleotides 460 to 481 of SEQ ID NO:1, nucleotides 461 to 482 of SEQ ID NO:1, nucleotides 462 to 483 of SEQ ID NO:1, nucleotides 463 to 484 of SEQ ID NO:1, nucleotides 464 to 485 of SEQ ID NO:1, nucleotides 465 to 486 of SEQ ID NO:1, nucleotides 466 to 487 of SEQ ID NO:1, nucleotides 467 to 488 of SEQ ID NO:1, nucleotides 468 to 489 of SEQ ID NO:1, nucleotides 469 to 490 of SEQ ID NO:1, nucleotides 470 to 491 of SEQ ID NO:1, nucleotides 471 to 492 of SEQ ID NO:1, nucleotides 472 to 493 of SEQ ID NO:1, nucleotides 473 to 494 of SEQ ID NO:1, nucleotides 474 to 495 of SEQ ID NO:1, nucleotides 475 to 496 of SEQ ID NO:1, nucleotides 476 to 497 of SEQ ID NO:1, nucleotides 477 to 498 of SEQ ID NO:1, nucleotides 478 to 499 of SEQ ID NO:1, nucleotides 479 to 500 of SEQ ID NO:1, nucleotides 480 to 501 of SEQ ID NO:1, nucleotides 481 to 502 of SEQ ID NO:1, nucleotides 482 to 503 of SEQ ID NO:1, nucleotides 483 to 504 of SEQ ID NO:1, nucleotides 484 to 505 of SEQ ID NO:1, nucleotides 485 to 506 of SEQ ID NO:1, nucleotides 486 to 507 of SEQ ID NO:1, nucleotides 487 to 508 of SEQ ID NO:1, nucleotides 488 to 509 of SEQ ID NO:1, nucleotides 489 to 510 of SEQ ID NO:1, nucleotides 490 to 511 of SEQ ID NO:1, nucleotides 491 to 512 of SEQ ID NO:1, nucleotides 492 to 513 of SEQ ID NO:1, nucleotides 493 to 514 of SEQ ID NO:1, nucleotides 494 to 515 of SEQ ID NO:1, nucleotides 495 to 516 of SEQ ID NO:1, nucleotides 496 to 517 of SEQ ID NO:1, nucleotides 497 to 518 of SEQ ID NO:1, nucleotides 498 to 519 of SEQ ID NO:1, nucleotides 499 to 520 of SEQ ID NO:1, and nucleotides 500 to 521 of SEQ ID NO:1.

As another example, pool of siRNA molecules of the invention derived from the *H. glycines* pas-5 gene, as set forth in SEQ ID NO:1, may comprise a multiplicity of RNA molecules substantially identical to nucleotides 501 to 522 of SEQ ID NO:1, nucleotides 502 to 523 of SEQ ID NO:1, nucleotides 503 to 524 of SEQ ID NO:1, nucleotides 504 to 525 of SEQ ID NO:1, nucleotides 505 to 526 of SEQ ID NO:1, nucleotides 506 to 527 of SEQ ID NO:1, nucleotides 507 to 528 of SEQ ID NO:1, nucleotides 508 to 529 of SEQ ID NO:1, nucleotides 509 to 530 of SEQ ID NO:1, nucleotides 510 to 531 of SEQ ID NO:1, nucleotides 511 to 532 of SEQ ID NO:1, nucleotides 512 to 533 of SEQ ID NO:1, nucleotides 513 to 534 of SEQ ID NO:1, nucleotides 514 to 535 of SEQ ID NO:1, nucleotides 515 to 536 of SEQ ID NO:1, nucleotides 516 to 537 of SEQ ID NO:1, nucleotides 517 to 538 of SEQ ID NO:1, nucleotides 518 to 539 of SEQ ID NO:1, nucleotides 519 to 540 of SEQ ID NO:1, nucleotides 520 to 541 of SEQ ID NO:1, nucleotides 521 to 542 of SEQ ID NO:1, nucleotides 522 to 543 of SEQ ID NO:1, nucleotides 523 to 544 of SEQ ID NO:1; nucleotides 524 to 545 of SEQ ID NO:1, nucleotides 525 to 546 of SEQ ID NO:1, nucleotides 526 to 547 of SEQ ID NO:1, nucleotides 527 to 548 of SEQ ID NO:1, nucleotides 528 to 549 of SEQ ID NO:1, nucleotides 529 to 550 of SEQ ID NO:1, nucleotides 530 to 551 of SEQ ID NO:1, nucleotides 531 to 552 of SEQ ID NO:1, nucleotides 532 to 553 of SEQ ID NO:1, nucleotides 533 to 554 of SEQ ID NO:1, nucleotides 534 to 555 of SEQ ID NO:1, nucleotides 535 to 556 of SEQ ID NO:1, nucleotides 536 to 557 of SEQ ID NO:1, nucleotides 537 to 558 of SEQ ID NO:1, nucleotides 538 to 559 of SEQ ID NO:1, nucleotides 539 to 560 of SEQ ID NO:1, nucleotides 540 to 561 of SEQ ID NO:1, nucleotides 541 to 562 of SEQ ID NO:1, nucleotides 542 to 563 of SEQ ID NO:1, nucleotides 543 to 564 of SEQ ID NO:1, nucleotides 544 to 565 of SEQ ID NO:1, nucleotides 545 to 566 of SEQ ID NO:1, nucleotides 546 to 567 of SEQ ID NO:1, nucleotides 547 to 568 of SEQ ID NO:1, nucleotides 548 to 569 of SEQ ID NO:1, nucleotides 549 to 570 of SEQ ID NO:1, and nucleotides 550 to 571 of SEQ ID NO:1.

As another example, a pool of siRNA molecules of the invention derived from the *H. glycines* pas-5 gene, as set forth in SEQ ID NO:1, may comprise a multiplicity of RNA molecules substantially identical to nucleotides 551 to 572 of SEQ ID NO:1, nucleotides 552 to 573 of SEQ ID NO:1, nucleotides 553 to 574 of SEQ ID NO:1, nucleotides 554 to 575 of SEQ ID NO:1, nucleotides 555 to 576 of SEQ ID NO:1, nucleotides 556 to 577 of SEQ ID NO:1, nucleotides 557 to 578 of SEQ ID NO:1, nucleotides 558 to 579 of SEQ ID NO:1, nucleotides 559 to 580 of SEQ ID NO:1, nucleotides 560 to 581 of SEQ ID NO:1, nucleotides 561 to 582 of SEQ ID NO:1, nucleotides 562 to 583 of SEQ ID NO:1, nucleotides 563 to 584 of SEQ ID NO:1, nucleotides 564 to 585 of SEQ ID NO:1, nucleotides 565 to 586 of SEQ ID NO:1, nucleotides 566 to 587 of SEQ ID NO:1, nucleotides 567 to 588 of SEQ ID NO:1, nucleotides 568 to 589 of SEQ ID NO:1, nucleotides 569 to 590 of SEQ ID NO:1, nucleotides 570 to 591 of SEQ ID NO:1, nucleotides 571 to 592 of SEQ ID NO:1, nucleotides 572 to 593 of SEQ ID NO:1, nucleotides 573 to 594 of SEQ ID NO:1, nucleotides 574 to 595 of SEQ ID NO:1, nucleotides 575 to 596 of SEQ ID NO:1, nucleotides 576 to 597 of SEQ ID NO:1, nucleotides 577 to 598 of SEQ ID NO:1, nucleotides 578 to 599 of SEQ ID NO:1, nucleotides 579 to 600 of SEQ ID NO:1, nucleotides 580 to 601 of SEQ ID NO:1, nucleotides 581 to 602 of SEQ ID NO:1, nucleotides 582 to 603 of SEQ ID NO:1, nucleotides 583 to 604 of SEQ ID NO:1, nucleotides 584 to 605 of SEQ ID NO:1, nucleotides 585 to 606 of SEQ ID NO:1, nucleotides 586 to 607 of SEQ ID NO:1, nucleotides 587 to 608 of SEQ ID NO:1, nucleotides 588 to 609 of SEQ ID NO:1, nucleotides 589 to 610 of SEQ ID NO:1, nucleotides 590 to 611 of SEQ ID NO:1, nucleotides 591 to 612 of SEQ ID NO:1, nucleotides 592 to 613 of SEQ ID NO:1, nucleotides 593 to 614 of SEQ ID NO:1, nucleotides 594 to 615 of SEQ ID NO:1, nucleotides 595 to 616 of SEQ ID NO:1, nucleotides 596 to 617 of SEQ ID NO:1, nucleotides 597 to 618 of SEQ ID NO:1, nucleotides 598 to 619 of SEQ ID NO:1, nucleotides 599 to 620 of SEQ ID NO:1, and nucleotides 600 to 621 of SEQ ID NO:1.

As another example, a pool of siRNA molecules of the invention derived from the *H. glycines* pas-5 gene as set forth in SEQ ID NO:1, may comprise a multiplicity of RNA molecules substantially identical to nucleotides 601 to 622 of SEQ ID NO:1, nucleotides 602 to 623 of SEQ ID NO:1, nucleotides 603 to 624 of SEQ ID NO:1, nucleotides 604 to 625 of SEQ ID NO:1, nucleotides 605 to 626 of SEQ ID NO:1, nucleotides 606 to 627 of SEQ ID NO:1, nucleotides 607 to 628 of SEQ ID NO:1, nucleotides 608 to 629 of SEQ ID NO:1, nucleotides 609 to 630 of SEQ ID NO:1, nucleotides 610 to 631 of SEQ ID NO:1, nucleotides 611 to 632 of SEQ ID NO:1, nucleotides 612 to 633 of SEQ ID NO:1, nucleotides 613 to 634 of SEQ ID NO:1, nucleotides 614 to 635 of SEQ ID NO:1, nucleotides 615 to 636 of SEQ ID NO:1, nucleotides 616 to 637 of SEQ ID NO:1, nucleotides 617 to 638 of SEQ ID NO:1, nucleotides 618 to 639 of SEQ ID NO:1, nucleotides 619 to 640 of SEQ ID NO:1, nucleotides 620 to 641 of SEQ ID NO:1, nucleotides 621 to 642 of SEQ ID NO:1, nucleotides 622 to 643 of SEQ ID NO:1, nucleotides 623 to 644 of SEQ ID NO:1, nucleotides 624 to 645 of SEQ ID NO:1, nucleotides 625 to 646 of SEQ ID NO:1, nucleotides 626 to 647 of SEQ ID NO:1, nucleotides 627 to 648 of SEQ ID NO:1, nucleotides 628 to 649 of SEQ ID NO:1, nucleotides 629 to 650 of SEQ ID NO:1, nucleotides 630 to 651 of SEQ ID NO:1, nucleotides 631 to 652 of SEQ ID NO:1, nucleotides 632 to 653 of SEQ ID NO:1, nucleotides 633 to 654 of SEQ ID NO:1, nucleotides 634 to 655 of SEQ ID NO:1, nucleotides 635 to 656 of SEQ ID NO:1, nucleotides 636 to 657 of SEQ ID NO:1, nucleotides 637 to 658 of SEQ ID NO:1, nucleotides 638 to 659 of SEQ ID NO:1, nucleotides 639 to 660 of SEQ ID NO:1, nucleotides 640 to 661 of SEQ ID NO:1, nucleotides 641 to 662 of SEQ ID NO:1, nucleotides 642 to 663 of SEQ ID NO:1, nucleotides 643 to 664 of SEQ ID NO:1, nucleotides 644 to 665 of SEQ ID NO:1, nucleotides 645 to 666 of SEQ ID NO:1, nucleotides 646 to 667 of SEQ ID NO:1, nucleotides 647 to 668 of SEQ ID NO:1, nucleotides 648 to 669 of SEQ ID NO:1, nucleotides 649 to 670 of SEQ ID NO:1, and nucleotides 650 to 671 of SEQ ID NO:1.

As another example, a pool of siRNA molecules of the invention derived from the *H. glycines* pas-5 gene, as set forth in SEQ ID NO:1, may comprise a multiplicity of RNA molecules substantially identical to nucleotides 651 to 672 of SEQ ID NO:1, nucleotides 652 to 673 of SEQ ID NO:1, nucleotides 653 to 674 of SEQ ID NO:1, nucleotides 654 to 675 of SEQ ID NO:1, nucleotides 655 to 676 of SEQ ID NO:1, nucleotides 656 to 677 of SEQ ID NO:1, nucleotides 657 to 678 of SEQ ID NO:1, nucleotides 658 to 679 of SEQ ID NO:1, nucleotides 659 to 680 of SEQ ID NO:1, nucleotides 660 to 681 of SEQ ID NO:1, nucleotides 661 to 682 of SEQ ID NO:1, nucleotides 662 to 683 of SEQ ID NO:1, nucleotides 663 to 684 of SEQ ID NO:1, nucleotides 664 to 685 of SEQ ID NO:1, nucleotides 665 to 686 of SEQ ID NO:1, nucleotides 666 to 687 of SEQ ID NO:1, nucleotides 667 to 688 of SEQ ID NO:1, nucleotides 668 to 689 of SEQ ID NO:1, nucleotides 669 to 690 of SEQ ID NO:1, nucleotides 670 to 691 of SEQ ID NO:1, nucleotides 671 to 692 of SEQ ID NO:1, nucleotides 672 to 693 of SEQ ID NO:1, nucleotides 673 to 694 of SEQ ID NO:1, nucleotides 674 to 695 of SEQ ID NO:1, nucleotides 675 to 696 of SEQ ID NO:1, nucleotides 676 to 697 of SEQ ID NO:1, nucleotides 677 to 698 of SEQ ID NO:1, nucleotides 678 to 699 of SEQ ID NO:1, nucleotides 679 to 700 of SEQ ID NO:1, nucleotides 680 to 701 of SEQ ID NO:1, nucleotides 681 to 702 of SEQ ID NO:1, nucleotides 682 to 703 of SEQ ID NO:1, nucleotides 683 to 704 of SEQ ID NO:1, nucleotides 684 to 705 of SEQ ID NO:1, nucleotides 685 to 706 of SEQ ID NO:1, nucleotides 686 to 707 of SEQ ID NO:1, nucleotides 687 to 708 of SEQ ID NO:1, nucleotides 688 to 709 of SEQ ID NO:1, nucleotides 689 to 710 of SEQ ID NO:1, nucleotides 690 to 711 of SEQ ID NO:1, nucleotides 691 to 712 of SEQ ID NO:1, nucleotides 692 to 713 of SEQ ID NO:1, nucleotides 693 to 714 of SEQ ID NO:1, nucleotides 694 to 715 of SEQ ID NO:1, nucleotides 695 to 716 of SEQ ID NO:1, nucleotides 696 to 717 of SEQ ID NO:1, nucleotides 697 to 718 of SEQ ID NO:1, nucleotides 698 to 719 of SEQ ID NO:1, nucleotides 699 to 720 of SEQ ID NO:1, and nucleotides 700 to 721 of SEQ ID NO:1.

As another example, a pool of siRNA molecules of the invention derived from the *H. glycines* pas-5 gene, as set forth in SEQ ID NO:1, may comprise a multiplicity of RNA molecules substantially identical to nucleotides 701 to 722 of SEQ ID NO:1, nucleotides 702 to 723 of SEQ ID NO:1, nucleotides 703 to 724 of SEQ ID NO:1, nucleotides 704 to 725 of SEQ ID NO:1, nucleotides 705 to 726 of SEQ ID NO:1, nucleotides 706 to 727 of SEQ ID NO:1, nucleotides 707 to 728 of SEQ ID NO:1, nucleotides 708 to 729 of SEQ ID NO:1, nucleotides 709 to 730 of SEQ ID NO:1, nucleotides 710 to 731 of SEQ ID NO:1, nucleotides 711 to 732 of SEQ ID NO:1, nucleotides 712 to 733 of SEQ ID NO:1, nucleotides 713 to 734 of SEQ ID NO:1, nucleotides 714 to 735 of SEQ ID NO:1, nucleotides 715 to 736 of SEQ ID NO:1, nucleotides 716 to 737 of SEQ ID NO:1, nucleotides 717 to 738 of SEQ ID NO:1, nucleotides 718 to 739 of SEQ ID NO:1, nucleotides 719 to 740 of SEQ ID NO:1, nucleotides 720 to 741 of SEQ ID NO:1, nucleotides 721 to 742 of SEQ ID NO:1, nucleotides 722 to 743 of SEQ ID NO:1, nucleotides 723 to 744 of SEQ ID NO:1, nucleotides 724 to 745 of SEQ ID NO:1, nucleotides 725 to 746 of SEQ ID NO:1, nucleotides 726 to 747 of SEQ ID NO:1, nucleotides 727 to 748 of SEQ ID NO:1, nucleotides 728 to 749 of SEQ ID NO:1, nucleotides 729 to 750 of SEQ ID NO:1, nucleotides 730 to 751 of SEQ ID NO:1, nucleotides 731 to 752 of SEQ ID NO:1, nucleotides 732 to 753 of SEQ ID NO:1, nucleotides 733 to 754 of SEQ ID NO:1, nucleotides 734 to 755 of SEQ ID NO:1, nucleotides 735 to 756 of SEQ ID NO:1, nucleotides 736 to 757 of SEQ ID NO:1, nucleotides 737 to 758 of SEQ ID NO:1, nucleotides 738 to 759 of SEQ ID NO:1, nucleotides 739 to 760 of SEQ ID NO:1, nucleotides 740 to 761 of SEQ ID NO:1, nucleotides 741 to 762 of SEQ ID NO:1, nucleotides 742 to 763 of SEQ ID NO:1, nucleotides 743 to 764 of SEQ ID NO:1, nucleotides 744 to 765 of SEQ ID NO:1, nucleotides 745 to 766 of SEQ ID NO:1, nucleotides 746 to 767 of SEQ ID NO:1, nucleotides 747 to 768 of SEQ ID NO:1, nucleotides 748 to 769 of SEQ ID NO:1, nucleotides 749 to 770 of SEQ ID NO:1, and nucleotides 750 to 771 of SEQ ID NO:1.

As another example, a pool of siRNA molecules of the invention derived from the *H. glycines* pas-5 gene, as set forth in SEQ ID NO:1, may comprise a multiplicity of RNA molecules substantially identical to nucleotides 751 to 772 of SEQ ID NO:1, nucleotides 752 to 773 of SEQ ID NO:1, nucleotides 753 to 774 of SEQ ID NO:1, nucleotides 754 to 775 of SEQ ID NO:1, nucleotides 755 to 776 of SEQ ID NO:1, nucleotides 756 to 777 of SEQ ID NO:1, nucleotides 757 to 778 of SEQ ID NO:1, nucleotides 758 to 779 of SEQ ID NO:1, nucleotides 759 to 780 of SEQ ID NO:1, nucleotides 760 to 781 of SEQ ID NO:1, nucleotides 761 to 782 of SEQ ID NO:1, nucleotides 762 to 783 of SEQ ID NO:1, nucleotides 763 to 784 of SEQ ID NO:1, nucleotides 764 to 785 of SEQ ID NO:1, nucleotides 765 to 786 of SEQ ID NO:1, nucleotides 766 to 787 of SEQ ID NO:1, nucleotides 767 to 788 of SEQ ID NO:1, nucleotides 768 to 789 of SEQ ID NO:1, nucleotides 769 to 790 of SEQ ID NO:1, nucleotides 770 to 791 of SEQ ID NO:1, nucleotides 771 to 792 of SEQ ID NO:1, nucleotides 772 to 793 of SEQ ID NO:1, nucleotides 773 to 794 of SEQ ID NO:1, nucleotides 774 to 795 of SEQ ID NO:1, nucleotides 775 to 796 of SEQ ID NO:1, nucleotides 776 to 797 of SEQ ID NO:1, nucleotides 777 to 798 of SEQ ID NO:1, nucleotides 778 to 799 of SEQ ID NO:1, nucleotides 779 to 800 of SEQ ID NO:1, nucleotides 780 to 801 of SEQ ID NO:1, nucleotides 781 to 802 of SEQ ID NO:1, nucleotides 782 to 803 of SEQ ID NO:1, nucleotides 783 to 804 of SEQ ID NO:1, nucleotides 784 to 805 of SEQ ID NO:1, nucleotides 785 to 806 of SEQ ID NO:1, nucleotides 786 to 807 of SEQ ID NO:1, nucleotides 787 to 808 of SEQ ID NO:1, nucleotides 788 to 809 of SEQ ID NO:1, nucleotides 789 to 810 of SEQ ID NO:1, nucleotides 790 to 811 of SEQ ID NO:1, nucleotides 791 to 812 of SEQ ID NO:1, nucleotides 792 to 813 of SEQ ID NO:1, nucleotides 793 to 814 of SEQ ID NO:1, nucleotides 794 to 815 of SEQ ID NO:1, nucleotides 795 to 816 of SEQ ID NO:1, nucleotides 796 to 817 of SEQ ID NO:1, nucleotides 797 to 818 of SEQ ID NO:1, nucleotides 798 to 819 of SEQ ID NO:1, nucleotides 799 to 820 of SEQ ID NO:1, and nucleotides 800 to 821 of SEQ ID NO:1.

As another example, a pool of siRNA molecules of the invention derived from the *H. glycines* pas-5 gene, as set forth in SEQ ID NO:1, may comprise a multiplicity of RNA molecules substantially identical to nucleotides 801 to 822 of SEQ ID NO:1, nucleotides 802 to 823 of SEQ ID NO:1, nucleotides 803 to 824 of SEQ ID NO:1, nucleotides 804 to 825 of SEQ ID NO:1, nucleotides 805 to 826 of SEQ ID NO:1, nucleotides 806 to 827 of SEQ ID NO:1, nucleotides 807 to 828 of SEQ ID NO:1, nucleotides 808 to 829 of SEQ ID NO:1, nucleotides 809 to 830 of SEQ ID NO:1, nucleotides 810 to 831 of SEQ ID NO:1, nucleotides 811 to 832 of SEQ ID NO:1, nucleotides 812 to 833 of SEQ ID NO:1, nucleotides 813 to 834 of SEQ ID NO:1, nucleotides 814 to 835 of SEQ ID NO:1, nucleotides 815 to 836 of SEQ ID NO:1, nucleotides 816 to 837 of SEQ ID NO:1, nucleotides 817 to 838 of SEQ ID NO:1, nucleotides 818 to 839 of SEQ ID NO:1, nucleotides 819 to 840 of SEQ ID NO:1, nucleotides 820 to 841 of SEQ ID NO:1, nucleotides 821 to 842 of SEQ ID NO:1, nucleotides 822 to 843 of SEQ ID NO:1, nucleotides 823 to 844 of SEQ ID NO:1, nucleotides 824 to 845 of SEQ ID NO:1, nucleotides 825 to 846 of SEQ ID NO:1, nucleotides 826 to 847 of SEQ ID NO:1, nucleotides 827 to 848 of SEQ ID NO:1, nucleotides 828 to 849 of SEQ ID NO:1, nucleotides 829 to 850 of SEQ ID NO:1, nucleotides 830 to 851 of SEQ ID NO:1, nucleotides 831 to 852 of SEQ ID NO:1, nucleotides 832 to 853 of SEQ ID NO:1, nucleotides 833 to 854 of SEQ ID NO:1, nucleotides 834 to 855 of SEQ ID NO:1, nucleotides 835 to 856 of SEQ ID NO:1, nucleotides 836 to 857 of SEQ ID NO:1, nucleotides 837 to 858 of SEQ ID NO:1, nucleotides 838 to 859 of SEQ ID NO:1, nucleotides 839 to 860 of SEQ ID NO:1, nucleotides 840 to 861 of SEQ ID NO:1, nucleotides 841 to 862 of SEQ ID NO:1, nucleotides 842 to 863 of SEQ ID NO:1, nucleotides 843 to 864 of SEQ ID NO:1, nucleotides 844 to 865 of SEQ ID NO:1, nucleotides 845 to 866 of SEQ ID NO:1, nucleotides 846 to 867 of SEQ ID NO:1, nucleotides 847 to 868 of SEQ ID NO:1, nucleotides 848 to 869 of SEQ ID NO:1, nucleotides 849 to 870 of SEQ ID NO:1, and nucleotides 850 to 871 of SEQ ID NO:1.

As another example, a pool of siRNA molecules of the invention derived from the *H. glycines* pas-5 gene, as set forth in SEQ ID NO:1, may comprise a multiplicity of RNA molecules substantially identical to nucleotides 851 to 872 of SEQ ID NO:1, nucleotides 852 to 873 of SEQ ID NO:1, nucleotides 853 to 874 of SEQ ID NO:1, nucleotides 854 to 875 of SEQ ID NO:1, nucleotides 855 to 876 of SEQ ID NO:1, nucleotides 856 to 877 of SEQ ID NO:1, nucleotides 857 to 878 of SEQ ID NO:1, nucleotides 858 to 879 of SEQ ID NO:1, nucleotides 859 to 880 of SEQ ID NO:1, nucleotides 860 to 881 of SEQ ID NO:1, nucleotides 861 to 882 of SEQ ID NO:1, nucleotides 862 to 883 of SEQ ID NO:1, nucleotides 863 to 884 of SEQ ID NO:1, nucleotides 864 to 885 of SEQ ID NO:1, nucleotides 865 to 886 of SEQ ID NO:1, nucleotides 866 to 887 of SEQ ID NO:1, nucleotides 867 to 888 of SEQ ID NO:1, nucleotides 868 to 889 of SEQ ID NO:1, nucleotides 869 to 890 of SEQ ID NO:1, nucleotides 870 to 891 of SEQ ID NO:1, nucleotides 871 to 892 of SEQ ID NO:1, nucleotides 872 to 893 of SEQ ID NO:1, nucleotides 873 to 894 of SEQ ID NO:1, nucleotides 874 to 895 of SEQ ID NO:1, nucleotides 875 to 896 of SEQ ID NO:1, nucleotides 876 to 897 of SEQ ID NO:1, nucleotides 877 to 898 of SEQ ID NO:1, nucleotides 878 to 899 of SEQ ID NO:1, nucleotides 879 to 900 of SEQ ID NO:1, nucleotides 880 to 901 of SEQ ID NO:1, nucleotides 881 to 902 of SEQ ID NO:1, nucleotides 882 to 903 of SEQ ID NO:1, nucleotides 883 to 904 of SEQ ID NO:1, nucleotides 884 to 905 of SEQ ID NO:1, nucleotides 885 to 906 of SEQ ID NO:1, nucleotides 886 to 907 of SEQ ID NO:1, nucleotides 887 to 908 of SEQ ID NO:1, nucleotides 888 to 909 of SEQ ID NO:1, nucleotides 889 to 910 of SEQ ID NO:1, nucleotides 890 to 911 of SEQ ID NO:1, nucleotides 891 to 912 of SEQ ID NO:1, nucleotides 892 to 913 of SEQ ID NO:1, nucleotides 893 to 914 of SEQ ID NO:1, nucleotides 894 to 915 of SEQ ID NO:1, nucleotides 895 to 916 of SEQ ID NO:1, nucleotides 896 to 917 of SEQ ID NO:1, nucleotides 897 to 918 of SEQ ID NO:1, nucleotides 898 to 919 of SEQ ID NO:1, nucleotides 899 to 920 of SEQ ID NO:1, and nucleotides 900 to 921 of SEQ ID NO:1.

As another example, a pool of siRNA molecules of the invention derived from the *H. glycines* pas-5 gene, as set forth in SEQ ID NO:1, may comprise a multiplicity of RNA molecules substantially identical to nucleotides 901 to 922 of SEQ ID NO:1, nucleotides 902 to 923 of SEQ ID NO:1; nucleotides 903 to 924 of SEQ ID NO:1, nucleotides 904 to 925 of SEQ ID NO:1, nucleotides 905 to 926 of SEQ ID NO:1, nucleotides 906 to 927 of SEQ ID NO:1, nucleotides 907 to 928 of SEQ ID NO:1, nucleotides 908 to 929 of SEQ ID NO:1, nucleotides 909 to 930 of SEQ ID NO:1, nucleotides 910 to 931 of SEQ ID NO:1, nucleotides 911 to 932 of SEQ ID NO:1, nucleotides 912 to 933 of SEQ ID NO:1, nucleotides 913 to 934 of SEQ ID NO:1, nucleotides 914 to 935 of SEQ ID NO:1, nucleotides 915 to 936 of SEQ ID NO:1, nucleotides 916 to 937 of SEQ ID NO:1, nucleotides 917 to 938 of SEQ ID NO:1, nucleotides 918 to 939 of SEQ ID NO:1, nucleotides 919 to 940 of SEQ ID NO:1, nucleotides 920 to 941 of SEQ ID NO:1, nucleotides 921 to 942 of SEQ ID NO:1, nucleotides 922 to 943 of SEQ ID NO:1, nucleotides 923 to 944 of SEQ ID NO:1, nucleotides 924 to 945 of SEQ ID NO:1, nucleotides 925 to 946 of SEQ ID NO:1, nucleotides 926 to 947 of SEQ ID NO:1, nucleotides 927 to 948 of SEQ ID NO:1, nucleotides 928 to 949 of SEQ ID NO:1, nucleotides 929 to 950 of SEQ ID NO:1, nucleotides 930 to 951 of SEQ ID NO:1, nucleotides 931 to 952 of SEQ ID NO:1, nucleotides 932 to 953 of SEQ ID NO:1, nucleotides 933 to 954 of SEQ ID NO:1, nucleotides 934 to 955 of SEQ ID NO:1, nucleotides 935 to 956 of SEQ ID NO:1, nucleotides 936 to 957 of SEQ ID NO:1, nucleotides 937 to 958 of SEQ ID NO:1, nucleotides 938 to 959 of SEQ ID NO:1, nucleotides 939 to 960 of SEQ ID NO:1, nucleotides 940 to 961 of SEQ ID NO:1, nucleotides 941 to 962 of SEQ ID NO:1, nucleotides 942 to 963 of SEQ ID NO:1, nucleotides 943 to 964 of SEQ ID NO:1, nucleotides 944 to 965 of SEQ ID NO:1, nucleotides 945 to 966 of SEQ ID NO:1, nucleotides 946 to 967 of SEQ ID NO:1, nucleotides 947 to 968 of SEQ ID NO:1, nucleotides 948 to 969 of SEQ ID NO:1, nucleotides 949 to 970 of SEQ ID NO:1, nucleotides 950 to 971 of SEQ ID NO:1, nucleotides 951 to 972 of SEQ ID NO:1, nucleotides 952 to 973 of SEQ ID NO:1, nucleotides 953 to 974 of SEQ ID NO:1, nucleotides 954 to 975 of SEQ ID NO:1, nucleotides 955 to 976 of SEQ ID NO:1, nucleotides 956 to 977 of SEQ ID NO:1, and nucleotides 957 to 978 of SEQ ID NO:1.

A pool of siRNA of the invention derived from the *H. glycines* pas-5 gene of SEQ ID NO:1 may also comprise any combination of RNA molecules having the specific 21 contiguous nucleotide sequences derived from SEQ ID NO:1 set forth above. Similarly, a pool of siRNA of the invention may comprise a multiplicity of RNA molecules having any 1 g contiguous nucleotide sequences derived from SEQ ID NO:1, or a multiplicity of RNA molecules having any 20 contiguous nucleotide sequences derived from SEQ ID NO:1. Alternatively, the pool of siRNA of the invention may comprise a multiplicity of RNA molecules having a combination of any 19, 20, and/or 21 contiguous nucleotide sequences derived from SEQ ID NO:1.

dsRNA containing a nucleotide sequence identical to a portion of the target gene is preferred for inhibition. As disclosed herein, 100% sequence identity between the RNA and the target gene is not required to practice the present invention. Thus, the invention has the advantage of being able to tolerate sequence variations that might be expected due to genetic mutation, strain polymorphism, or evolutionary divergence. RNA sequences with insertions, deletions, and single point mutations relative to the target sequence may also be effective for inhibition. Thus, sequence identity may optimized by sequence comparison and alignment algorithms known in the art (see Gribskov and Devereux, Sequence Analysis Primer, Stockton Press, 1991, and references cited therein) and calculating the percent difference between the nucleotide sequences by, for example, the Smith-Waterman algorithm as implemented in the BESTFIT software program using default parameters (e.g., University of Wisconsin Genetic Computing Group). Greater than 90% sequence identity, or even 100% sequence identity, between the inhibitory RNA and the portion of the target gene is preferred. Alternatively, the duplex region of the RNA may be defined functionally as a nucleotide sequence that is capable of hybridizing with a portion of the target gene transcript under stringent conditions (e.g., 400 mM NaCl, 40 mM PIPES pH 6.4, 1 mM EDTA, 60° C. hybridization for 12-16 hours; followed by washing). The length of the substantially identical double-stranded nucleotide sequences may be at least about 21, 25, 50, 100, 200, 300, 400, 500, 600, 700, or 978 bases. In a preferred embodiment, the length of the double-stranded nucleotide sequence is from approximately from about 21 to about 400 or 500 nucleotides in length.

Preferably, the dsRNA molecule of the present invention comprises one strand comprising a sequence substantially identical to a portion of a target gene from any parasitic nematode. Suitable parasitic nematode target genes are at least about 50-60%, preferably at least about 60-70%, and more preferably at least about 70-75%, 75-80%, 80-85%, 85-90%, or 90-95%, and most preferably at least about 96%, 97%, 98%, 99%, or more identical to a polynucleotide comprising the sequence set forth in SEQ ID NO:1. Alternatively, suitable parasitic nematode target genes comprise a polynucleotide from a parasitic plant nematode that hybridizes under stringent conditions to a polynucleotide comprising the sequence set forth in SEQ ID NO:1.

The dsRNA of the invention may optionally comprise a single stranded overhang at either or both ends. The double-stranded structure may be formed by a single self-complementary RNA strand (i.e. forming a hairpin loop) or two complementary RNA strands. RNA duplex formation may be initiated either inside or outside the cell. When the dsRNA of the invention forms a hairpin loop, it may optionally comprise an intron, as set forth in U.S. 2003/0180945A1 or a nucleotide spacer, which is a stretch of sequence between the complementary RNA strands to stabilize the hairpin transgene in cells. Methods for making various dsRNA molecules are set forth, for example, in WO 99/53050 and in U.S. Pat. No. 6,506,559. The RNA may be introduced in an amount that allows delivery of at least one copy per cell. Higher doses of double-stranded material may yield more effective inhibition.

In another embodiment, the invention provides an isolated recombinant expression vector comprising a nucleic acid encoding a dsRNA molecule as described above, wherein expression of the vector in a host plant cell results in increased resistance to a parasitic nematode as compared to a wild-type variety of the host plant cell. As used herein, the term "vector" refers to a nucleic acid molecule capable of transporting another nucleic acid to which it has been linked. One type of vector is a "plasmid," which refers to a circular double stranded DNA loop into which additional DNA segments can be ligated. Another type of vector is a viral vector, wherein additional DNA segments can be ligated into the viral genome. Certain vectors are capable of autonomous replication in a host plant cell into which they are introduced. Other vectors are integrated into the genome of a host plant cell upon introduction into the host cell, and thereby are replicated along with the host genome. Moreover, certain vectors are capable of directing the expression of genes to which they are operatively linked. Such vectors are referred to herein as "expression vectors." In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., potato virus X, tobacco rattle virus, and Geminivirus), which serve equivalent functions.

The recombinant expression vectors of the invention comprise a nucleic acid of the invention in a form suitable for expression of the nucleic acid in a host plant cell, which means that the recombinant expression vector includes one or more regulatory sequences, selected on the basis of the host plant cells to be used for expression, which is operatively linked to the nucleic acid sequence to be expressed. With respect to a recombinant expression vector, "operatively linked" is intended to mean that the nucleotide sequence of interest is linked to the regulatory sequence(s) in a manner which allows for expression of the nucleotide sequence (e.g., in a host plant cell when the vector is introduced into the host plant cell). The term "regulatory sequence" is intended to include promoters, enhancers, and other expression control elements (e.g., polyadenylation signals). Such regulatory sequences are described, for example, in Goeddel, Gene Expression Technology: Methods in Enzymology 185, Academic Press, San Diego, Calif. (1990) and Gruber and Crosby, in: Methods in Plant Molecular Biology and Biotechnology, Eds. Glick and Thompson, Chapter 7, 89-108, CRC Press: Boca Raton, Fla., including the references therein. Regulatory sequences include those that direct constitutive expression of a nucleotide sequence in many types of host cells and those that direct expression of the nucleotide sequence only in certain host cells or under certain conditions. It will be appreciated by those skilled in the art that the design of the expression vector can depend on such factors as the choice of the host cell to be transformed, the level of expression of dsRNA desired, etc. The expression vectors of the invention can be introduced into plant host cells to thereby produce dsRNA molecules encoded by nucleic acids as described herein.

In accordance with the invention, the recombinant expression vector comprises a regulatory sequence operatively linked to a nucleotide sequence that is a template for one or both strands of the claimed dsRNA. In one embodiment, the nucleic acid molecule further comprises a promoter flanking either end of the nucleic acid molecule, wherein the promoters drive expression of each individual DNA strand, thereby generating two complementary RNAs that hybridize and form the dsRNA. In another embodiment, the nucleic acid molecule comprises a nucleotide sequence that is transcribed into both strands of the dsRNA on one transcription unit, wherein the sense strand is transcribed from the 5' end of the transcription unit and the antisense strand is transcribed from the 3' end, wherein the two strands are separated by 3 to 500 basepairs, and wherein after transcription, the RNA transcript folds on itself to form a hairpin. In accordance with the invention, the spacer region in the hairpin transcript may be any DNA fragment.

According to the present invention, the introduced polynucleotide may be maintained in the plant cell stably if it is incorporated into a non-chromosomal autonomous replicon or integrated into the plant chromosomes. Alternatively, the introduced polynucleotide may be present on an extra-chromosomal non-replicating vector and be transiently expressed or transiently active. Whether present in an extra-chromosomal non-replicating vector or a vector that is integrated into a chromosome, the polynucleotide preferably resides in a plant expression cassette. A plant expression cassette preferably contains regulatory sequences capable of driving gene expression in plant cells that are operatively linked so that each sequence can fulfill its function, for example, termination of transcription by polyadenylation signals. Preferred polyadenylation signals are those originating from *Agrobacterium tumefaciens* t-DNA such as the gene 3 known as octopine synthase of the Ti-plasmid pTiACH5 (Gielen et al., 1984, EMBO J. 3:835) or functional equivalents thereof, but also all other terminators functionally active in plants are suitable. As plant gene expression is very often not limited on transcriptional levels, a plant expression cassette preferably contains other operatively linked sequences like translational enhancers such as the overdrive-sequence containing the 5'-untranslated leader sequence from tobacco mosaic virus enhancing the polypeptide per RNA ratio (Gallie et al., 1987, Nucl. Acids Research 15:8693-8711). Examples of plant expression vectors include those detailed in: Becker, D. et al., 1992, New plant binary vectors with selectable markers located proximal to the left border, Plant Mol. Biol. 20:1195-1197; Bevan, M. W., 1984, Binary *Agrobacterium* vectors for plant transformation, Nucl. Acid. Res. 12:8711-8721; and Vectors for Gene Transfer in Higher Plants; in: Transgenic Plants, Vol. 1, Engineering and Utilization, eds.: Kung and R. Wu, Academic Press, 1993, S. 15-38.

Plant gene expression should be operatively linked to an appropriate promoter conferring gene expression in a timely, cell type-preferred, or tissue-preferred manner. Promoters useful in the expression cassettes of the invention include any promoter that is capable of initiating transcription in a plant cell present in the plant's roots. Such promoters include, but are not limited to those that can be obtained from plants, plant viruses and bacteria that contain genes that are expressed in plants, such as *Agrobacterium* and *Rhizobium*. Preferably, the expression cassette of the invention comprises a root-specific promoter or a parasitic nematode feeding cell-specific promoter.

The promoter may be constitutive, inducible, developmental stage-preferred, cell type-preferred, tissue-preferred or organ-preferred. Constitutive promoters are active under most conditions. Examples of constitutive promoters include the CaMV 195 and 35S promoters (Odell et al, 1985, Nature 313:810-812), the sX CaMV $^{35}$S promoter (Kay et al., 1987, Science 236:1299-1302), the Sep1 promoter, the rice actin promoter (McElroy et al., 1990, Plant Cell 2:163-171), the *Arabidopsis* actin promoter, the ubiquitin promoter (Christensen et al., 1989, Plant Molec. Biol. 18:675-689); pEmu (Last et al., 1991, Theor. Appl. Genet. 81:581-588), the figwort mosaic virus 35S promoter, the Smas promoter (Velten et al., 1984, EMBO J. 3:2723-2730), the GRP1-8 promoter, the cinnamyl alcohol dehydrogenase promoter (U.S. Pat. No. 5,683,439), promoters from the T-DNA of *Agrobacterium*, such as mannopine synthase, nopaline synthase, and octopine synthase, the small subunit of ribulose biphosphate carboxylase (ssuRUBISCO) promoter, and the like. Promoters that express the dsRNA in a cell that is contacted by parasitic nematodes are preferred. Alternatively, the promoter may drive expression of the dsRNA in a plant tissue remote from the site of contact with the nematode, and the dsRNA may then be transported by the plant to a cell that is contacted by the parasitic nematode.

Inducible promoters are active under certain environmental conditions, such as the presence or absence of a nutrient or metabolite, heat or cold, light, pathogen attack, anaerobic conditions, and the like. For example, the promoters TobRB7, AtRPE, AtPyk10, Gemini19, and AtHMG1 have been shown to be induced by nematodes (for a review of nematode-inducible promoters, see Ann. Rev. Phytopathol. (2002) 40:191-219; see also U.S. Pat. No. 6,593,513). Method for isolating additional promoters, which are inducible by nematodes are set forth in U.S. Pat. Nos. 5,589,622, and 5,824,876. Other inducible promoters include the hsp80 promoter from *Brassica* is induced by heat shock; the PPDK promoter is induced by light; the PR-1 promoter from tobacco, *Arabidopsis*, and maize are inducible by infection with a pathogen; and the Adh1 promoter is induced by hypoxia and cold stress. Plant gene expression can also be facilitated via an inducible promoter (For review, see Gatz, 1997, Annu. Rev. Plant Physiol. Plant Mol. Biol. 48:89-108). Chemically inducible promoters are especially suitable if time-specific gene expression is desired. Examples of such promoters are a salicylic acid inducible promoter (PCT Application No. WO 95/19443), a tetracycline inducible promoter (Gatz et al., 1992, Plant J. 2:397-404) and an ethanol inducible promoter (PCT Application No. WO 93/21334).

Developmental stage-preferred promoters are preferentially expressed at certain stages of development. Tissue and organ preferred promoters include those that are preferentially expressed in certain tissues or organs, such as leaves, roots, seeds, or xylem. Examples of tissue preferred and organ preferred promoters include, but are not limited to fruit-preferred, ovule-preferred, male tissue-preferred, seed-preferred, integument-preferred, tuber-preferred, stalk-preferred, pericarp-preferred, and leaf-preferred, stigma-preferred, pollen-preferred, anther-preferred, a petal-preferred, sepal-preferred, pedicel-preferred, silique-preferred, stem-preferred, root-preferred promoters and the like. Seed preferred promoters are preferentially expressed during seed development and/or germination. For example, seed preferred promoters can be embryo-preferred, endosperm preferred and seed coat-preferred. See Thompson et al., 1989, BioEssays 10:108. Examples of seed preferred promoters include, but are not limited to cellulose synthase (celA), Cim1, gamma-zein, globulin-1, maize 19 kD zein (cZ19B1) and the like.

Other suitable tissue-preferred or organ-preferred promoters include the napin-gene promoter from rapeseed (U.S. Pat. No. 5,608,152), the USP-promoter from *Vicia faba*(Baeumlein et al., 1991, Mol Gen Genet. 225(3):459-67), the oleosin-promoter from *Arabidopsis* (PCT Application No. WO 98/45461), the phaseolin-promoter from *Phaseolus vulgaris* (U.S. Pat. No. 5,504,200), the Bce4-promoter from *Brassica* (PCT Application No. WO 91/13980), or the legumin B4 promoter (LeB4; Baeumlein et al., 1992, Plant Journal, 2(2): 233-9), as well as promoters conferring seed specific expression in monocot plants like maize, barley, wheat, rye, rice, etc. Suitable promoters to note are the Ipt2 or Ipt1-gene promoter from barley (PCT Application No. WO 95/15389 and PCT Application No. WO 95/23230) or those described in PCT Application No. WO 99/16890 (promoters from the barley hordein-gene, rice glutelin gene, rice oryzin gene, rice prolamin gene, wheat gliadin gene, wheat glutelin gene, oat glutelin gene, *Sorghum* kasirin-gene, and rye secalin gene).

Other promoters useful in the expression cassettes of the invention include, but are not limited to, the major chlorophyll a/b binding protein promoter, histone promoters, the Ap3 promoter, the β-conglycin promoter, the napin promoter, the soybean lectin promoter, the maize 15 kD zein promoter, the 22 kD zein promoter, the 27 kD zein promoter, the g-zein promoter, the waxy, shrunken 1, shrunken 2, and bronze promoters, the Zm13 promoter (U.S. Pat. No. 5,086,169), the maize polygalacturonase promoters (PG) (U.S. Pat. Nos. 5,412,085 and 5,545,546), and the SGB6 promoter (U.S. Pat. No. 5,470,359), as well as synthetic or other natural promoters.

In accordance with the present invention, the expression cassette comprises an expression control sequence operatively linked to a nucleotide sequence that is a template for one or both strands of the dsRNA. The dsRNA template comprises (a) a first stand having a sequence substantially identical to from about 21 to about 400 or 500 consecutive nucleotides of SEQ ID NO:1; and (b) a second strand having a sequence substantially complementary to the first strand. In further embodiments, a promoter flanks either end of the template nucleotide sequence, wherein the promoters drive expression of each individual DNA strand, thereby generating two complementary RNAs that hybridize and form the dsRNA. In alternative embodiments, the nucleotide sequence is transcribed into both strands of the dsRNA on one transcription unit, wherein the sense strand is transcribed from the 5' end of the transcription unit and the antisense strand is transcribed from the 3' end, wherein the two strands are separated by 3 to 500 basepairs, and wherein after transcription, the RNA transcript folds on itself to form a hairpin.

The invention is also embodied in a transgenic plant capable of expressing the dsRNA of the invention and thereby inhibiting the target genes in parasitic nematodes. Suitable methods for transforming or transfecting host cells including plant cells can be found in Sambrook et al. (Molecular Cloning: A Laboratory Manual. 2$^{nd}$ Ed., Cold Spring Harbor Laboratory, Cold Spring Harbor Laboratory Press, Cold Spring Harbor, N.Y., 1989) and other laboratory manuals such as Methods in Molecular Biology, 1995, Vol. 44, *Agrobacterium* protocols, Ed: Gartland and Davey, Humana Press, Totowa, N.J. Any method may be used to transform the recombinant expression vector into plant cells to yield the transgenic plants of the invention. General methods for transforming dicotyledenous plants are disclosed, for example, in U.S. Pat. Nos. 4,940,838; 5,464,763, and the like. Methods for transforming specific dicotyledenous plants, for example, cotton, are set forth in U.S. Pat. Nos. 5,004,863; 5,159,135; and 5,846,797. Soybean transformation methods, as set forth in U.S. Pat. Nos. 4,992,375; 5,416,011; 5,569,834; 5,824,877; 6,384,301 and in EP 0301749B1, may be used. Other plant transformation methods are disclosed, for example, in U.S. Pat. Nos. 4,945,050; 5,188,958; 5,596,131; 5,981,840; and the like.

In accordance with this embodiment, the transgenic plant of the invention is produced by a method comprising the steps of providing a parasitic nematode pas-5 target gene, preparing an expression cassette having a first region that is substantially identical to a portion of the selected target gene and a second region which is complementary to the first region, transforming the expression cassette into a plant, and selecting progeny of the transformed plant which express the dsRNA construct of the invention.

As increased resistance to nematode infection is a general trait wished to be inherited into a wide variety of plants, including but not limited to soybean, maize, barley, canola, wheat, cotton, tobacco, sugarbeet, potato, tomato, cabbage, cucumber, pea, and lettuce. In a preferred embodiment, the plant is a soybean plant.

The present invention also provides a method for inhibiting expression of a parasitic nematode pas-5 target gene. In accordance with this embodiment, the method comprises the step of administering to the nematode a dsRNA in an amount sufficient to inhibit expression of the nucleic acid, wherein one strand of the dsRNA is substantially identical to a portion of SEQ ID Nos:1, 2, 3, or 4. Oligonucleotides corresponding to a parasitic nematode target gene nucleotide sequence, for use as dsRNA in accordance with the invention, can be prepared by standard synthetic techniques, e.g., using an automated DNA synthesizer.

Physical methods of introducing dsRNA into parasitic nematodes include injection of a solution containing the dsRNA or soaking the parasitic nematode in a solution of the dsRNA. Preferably, the dsRNA of the invention is introduced into parasitic nematodes when the nematodes ingest transgenic plants containing expression vectors encoding the dsRNA.

The following examples are not intended to limit the scope of the claims to the invention, but are rather intended to be exemplary of certain embodiments. Any variations in the exemplified methods that occur to the skilled artisan are intended to fall within the scope of the present invention.

EXAMPLE 1

Identification And Isolation Of *H. Glycines* pas-5 Target Gene

The target candidate gene was identified through intensive datamining of the GENBANK SCN EST and *C. elegans* databases. The criteria used for datamining include EST sequence assembling, blast searches, expression of SCN target genes in pre-parasitic J2 stages and parasitic stages, no or very low homology of SCN target genes to soybean endogenous genes at nucleotide levels, essentiality of *C. elegans* homologues and their suitability for RNAi by feeding. The definition of essentiality for a gene includes, for example, developmental defects, lethality and sterility when the target gene is down-regulated or knocked-out by RNAi.

Using total RNA isolated from SCN J2 stage, RT-PCR was used to isolate cDNA fragments that were approximately 400~500 bp in length. The PCR products were cloned into TOPO pCR2.1 vector (Invitrogen, Carlsbad, Calif.) and inserts were confirmed by sequencing. RT-PCR was performed using primer sets (SEQ ID NOs:8 and 9) and the SuperScript One-Step RT-PCR with Platinum Taq DNA Polymerase kit (Invitrogen, Carlsbad, Calif., cat. No. 10928-034). Briefly, total RNA was isolated from SCN J2 (race 3) using standard TRIzol method. RT-PCR reactions contained 0.5 μl SCN J2 total RNA (1 μg/μl), 0.5 μl forward primer (10 pmol/μl), 0.5 μl reverse primer (10 pmol/μl), 12.5 μl of 2× Reaction Mix, 10.5 μl of ddH2O, 0.5 μl of RT/Platinum Taq Mix in a total volume of 25.0 μl. The reactions were run on a thermal cycler for 30 minutes at 50° C.; followed by 29 cycles at 94° C. for 15 seconds; 55° C. for 30 seconds, 72° C. for 1 minute; followed by 72° C. for 10 minutes, and terminating at 4° C. A gene fragment represented by nucleotides 73-589 of SEQ ID NO:1 was isolated using this method, and determined to be a homolog of *C. elegans* pas-5. In order to obtain full-length cDNAs for *H. glycines* pas-5, the 5' and 3' cDNA ends of the gene were obtained using a RNA ligase-mediated rapid amplification (GeneRacer Kit by Invitrogen, Carlsbad, Calif., cat. No. L1500-01).

The GeneRacer kit for 5' rapid amplification of cDNA ends was initiated with the treatment of total RNA with calf intestinal phosphatase to remove the 5'phosphates from truncated mRNA and non-mRNA. The dephosphorylated RNA was then treated with tobacco acid pyrophophatase to remove of the 5'cap from full length mRNA, leaving an exposed 5'phosphate. The GeneRacer RNA Oligo was ligated to the 5'end of mature mRNA. The reverse-transcription reaction was carried out with SuperScript III RT and first-strand cDNA was created.

The initial PCR reaction was conducted using a GeneRacer RNA Oligo and a gene specific reverse primer (SEQ ID NOs: 3 and 10, respectively). A nested PCR reaction was subsequently performed using GeneRacer 5' nested primer and a gene specific reverse primer (SEQ ID NOs: 4 and 11, respectively). In both initial and nested PCR, HotStar Taq DNA polymerase (Qiagen, Valencia, Calif., catalog No. 203203) was used. The reactions were run on a thermal cycler for 15 minutes at 95° C.; followed by 35 cycles at 94° C. for 1 minute; 52° C. for 30 seconds, 72° C. for 2 minutes; followed by 72° C. for 10 minutes, and terminating at 4° C. PCR products were cloned into pCR4-TOPO (Invitrogen, Carlsbad, Calif.) and sequenced.

3'cDNA ends were amplified using the GeneRacer Kit (Invitrogen, Carlsbad, Calif., catalog No. L1500-01). The first-strand cDNAs were generated through reverse transcription using total RNA and the GeneRacer Oligo dT Primer (SEQ ID NO:7). The 3' RACE PCR was performed with the GeneRacer 3' Primer (SEQ ID NO:5) and a gene-specific forward primer (SEQ ID NO:12). The nested PCR reactions were subsequently conducted using GeneRacer 3' Nested Primer (SEQ ID NO:6) and a gene-specific forward primer (SEQ ID NO:13). The reactions were run on a thermal cycler for 2 minutes at 94° C.; followed by 5 cycles at 94° C. for 30 seconds, 72° C. for 1.5 minutes; followed by 5 cycles at 94° C. for 30 seconds, 70° C. for 1.5 minutes; followed by 25 cycles at 94° C. for 30 seconds, 60° C. for 30 seconds, 72° C. for 1.5 minutes; followed by 72° C. at 10 minutes, and terminating at 4° C. PCR products were cloned into pCR4-TOPO (Invitrogen, Carlsbad, Calif.) and sequenced.

The sequences of the pas-5 PCR fragments isolated above were assembled into a full-length cDNA corresponding to the gene designated *H. glycines* pas-5, and this sequence is set forth as SEQ ID NO:1.

EXAMPLE 2

Isolation And Demonstration Of Essentiality Of *C. Elegans* Homologs Of SCN Target Gene RNAi was discovered in the free-living model nematode *C. elegans* (Fire et al., *Nature* 391: 806-811, 1998). One of the methods for introducing dsRNA into *C. elegans* is to feed the nematodes with bacteria expressing dsRNA, as *C. elegans* uses bacteria as its food sources (Timmons and Fire, *Nature* 395, 854, 1998). This method is also analogous to the delivery of dsRNA into SCN through feeding cells, the nutrient sources for SCN provided by plant host.

The homolog of the SCN target gene identified in Example 1 was isolated from *C. elegans* using PCR primers (SEQ ID NOs:14 and 15 in FIG. 2) and *C. elegans* genomic DNA as a template. The PCR products (~1 kb in length) isolated from exon-rich regions of genomic DNA and were cloned into the multiple cloning site of pLitmus28i (New England Biolabs, Beverly, Mass.), so that *C. elegans* gene fragments were flanked by two T7 promoters in a head-to-head configuration. The DNA sequences of *C. elegans* gene fragment used in RNAi assay are shown in FIG. 3 (SEQ ID NO:16).

The pLitmus28i vectors with the target genes were then transformed into *E coli* strain HT115(DE3). This strain is deficient in RNase III—an enzyme that degrades dsRNA. Therefore, dsRNA produced in HT115(DE3) is expected to be more stable. Upon IPTG (Isopropyl β-D-Thiogalactopyranoside) induction, T7 RNA polymerase, which is integrated in the genome of HT115(DE3), expresses and binds to the T7 promoters and transcribes dsRNA. The production of dsRNA in *E. coli* was confirmed by total RNA extraction using RiboPure-Bacteria Kit (Ambion, Austin, Tex., cat no 1925) and subsequent S1 nuclease treatment.

Briefly, the *C. elegans* RNAi feeding assay consisted growing the HT115(DE3) cultures overnight, centrifuging the HT115(DE3) cultures at 3000 rpm for 10 minutes, discarding the supernatant and resuspending the pellet in 1 ml of Induction Buffer A at room temperature, overnight. Induction Buffer A consisted of 10 ml of S-Media (Sulston and Brenner, *Genetics* 77: 95-104, 1974), 10 µl of IPTG (100 mg/ml), and 1 µl of Carbenicillin (50 mg/ml). The cultures were then spun down at 3000 rpm for 10 minutes, the supernatant discarded, and the pellet resuspended in Induction Buffer B to $OD_{600}$ around 0.6. Induction Buffer B consisted of 10 ml of S-Media, 5 µl of IPTG (100 mg/ml), and 1 µl of Carbenicillin (50 mg/ml). In a 96 well microtiter plate, 50 µl of the *E. coli* cultures was added to each well. Approximately 3 µl of L1 larvae (10 to 15 L1 s) were then added to each well. L1 larvae were chosen for RNAi assay in order to identify genes essential for post-embryonic development of the nematode. The plate was transferred into a container with wet paper towels, and placed in an incubator at approximately 25° C. for 5 days. For each target gene, two independent transformed HT 115 (DE3) colonies were picked for making the cultures. Each culture was triplicated, so a total of six wells were used for each *C. elegans* gene tested in the assay. The bacteria transformed with pLitmus28i alone (no inserts) was used as the control. The assay was examined and RNAi phenotypes of the *C. elegans* were analyzed.

By Day 5, in the control (pLitmus28i alone), L1 larvae developed into gravid adults and produced many progeny. The administration by feeding dsRNA substantially identical to the *C. elegans* pas-5 target gene resulted in arrest in development of nematodes, and the worms in all six wells for the pas-5 target gene showed consistent RNAi phenotypes. dsRNA substantially identical to the pas-5 gene ((SEQ ID NO:16), the homolog of *H. glycines* pas-5 (SEQ ID NO:1)) caused lethality at the early larval stage. These data demonstrated that *C. elegans* homologue of the SCN target gene candidate identified in Example 1 is essential for *C. elegans* development. This further indicated that the selected target gene indeed plays a key role for nematode development in both SCN and *C. elegans*.

EXAMPLE 3

Binary Vector Construction For Soybean Transformation

In order to evaluate whether the SCN target is effective in vivo, cDNA fragments for the SCN target gene were used to make binary vectors. The vectors consist of an antisense fragment of the target *H. glycines* pas-5 gene, an intron or spacer, a sense fragment of target *H. glycines* pas-5 and a vector backbone. In such vectors, dsRNA for the *H. glycines* pas-5 gene was expressed under a Super promoter (Ni, M. et al., Plant Journal 7, 661-676, 1995). This promoter drives transgene expression at high level in many tissues including roots. The selection marker for transformation was a mutated AHAS gene from *Arabidopsis thaliana* that conferred tolerance to the herbicide ARSENAL (imazepyr, BASF Corporation, Mount Olive, N.J.). The expression of mutated AHAS was driven by the *Arabidopsis* actin 2 promoter. The pAW30 vector used as a control in the bioassay experiments set forth in Example 4 and in the molecular characterization experiments of Example 5 contained all of the elements described above, but did not contain sense or antisense fragments of a dsRNA transgene. A gene fragment corresponding to nucleotides 73-589 of SEQ ID NO:1 was used to construct the binary vector pWT087 shown in FIG. 4.

EXAMPLE 4

Generation Of Transgenic Soybean Hairy-root And Nematode Bioassay

The soybean cyst nematode can be propagated on normal soybean root explants. However, this technique requires the continual establishment of root explants because these organs have a determinant period of growth in culture. In contrast, soybean hairy roots generated by infecting soybean cotyledons with *A. rhizogenes* exhibit indeterminate growth in tissue culture providing an alternative to normal root explants for monoxenic propagation and study of soybean cyst nematode (Cho et. al., (1998) Plant Sci. 138, 53-65). The *A. rhizogenes* can transfer the T-DNA of binary vectors in trans, thereby enabling the production of transgenic hairy roots containing foreign genes inserted in the T-DNA plasmid. This method has been used to produce transgenic roots in several plant species (Christey, (1997) Doran, P. M. (ed) Hairy roots: culture and application, Harwood, Amsterdam, pp. 99-111). The transgenic hairy roots can then be used to study the effect of transgene expression on any given phenotype. In the present example, the transgenic hairy roots were used to study the effect of dsRNA generated from the pWT087 binary vector corresponding to the *H. glycines* target gene designated pas-5 (SEQ ID NO:1) in conferring cyst nematode resistance.

The binary vectors pWT087 and pAW30 were transformed into *A. rhizogenes* K599 strain by electroporation (Cho et al., supra). The transformed strains of *Agrobacterium* were used to induce soybean hairy-root formation using the following protocol. Briefly, approximately five days before *A. rhizogenes* inoculation, seeds from soybean cultivar Williams 82 (SCN-susceptible) were sterilized with 10% bleach for 10 min and germinated on 1% agar at 25° C. with 16 hour/day lighting. Approximately three days before *A. rhizogenes* inoculation, a frozen stock of *A. rhizogenes* Strain K599 containing the binary vector was streaked on LB+kanamycin (50 μg/ml) plates and incubated at 28° C. in darkness. Approximately one day before *A. rhizogenes* inoculation, a colony was picked from the plate and immersed into liquid LB+kanamycin (50 μg/ml). The culture was shaken at 28° C. for approximately 16 hours. The concentration of *A. rhizogenes* in the liquid culture was adjusted to $OD_{600}$=1.0. Cotyledons were excised from the soybean seedling and the adaxial side was wounded several times with a scalpel. 15 μl of *A. rhizogenes* suspension was inoculated onto the wounded surface, and the cotyledon was placed with the adaxial side up on a 1% agar plate for 3 days at 25° C. under 16 hour/day lighting. The cotyledons were then transferred onto MS plates containing 500 μg/ml Carbenicillin (to suppress *A. rhizogenes*) and 1 μM ARSENAL. After culturing the cotyledons on selection media for 2 weeks, hairy roots were induced from the wounding site. The roots tolerant to ARSENAL and growing on the selection media were harvested and transferred onto fresh selection media of the same composition and incubated at 25° C. in darkness. Two weeks after harvesting hairy roots and culturing them on selection media, the hairy roots were subcultured onto MS media containing Carbenicillin 500 μg/ml but not ARSENAL. Non-transgenic hairy roots from soybean cultivar Williams 82 (SCN susceptible) and Cyst X (SCN resistant) were also generated by using non-transformed *A. rhizogenes*, to serve as controls for nematode growth in the assay.

A bioassay to assess nematode resistance was performed on the transgenic hairy-root transformed with the vectors pWT087 and pAW30, and on non-transgenic hairy roots from Williams 82 and Cyst X as controls. Two-week old hairy root cultures of each line that occupied at least half of the plate were inoculated with surface-decontaminated race 3 of soybean cyst nematode (SCN) second stage juveniles (J2) at the level of 2500 J2/plate. The plates were then sealed and put back into the incubator at 25° C. in darkness. Several independent hairy root lines were generated from each binary vector transformation and the lines used for bioassay. As an example of the nomenclature used for the transgenic lines, WT87-L7 indicates Line 7 generated from transformation with pWT087. Four weeks after nematode inoculation, the cyst number in each plate was counted. For each line, several replicated plates (number of replicates indicated by n) were used and the average count (AVG), female index %, and standard error (SE) values calculated as shown in the Table below. Results in the Table represent data from the same bioassay experiment.

As shown in Table 1, transgenic lines transformed with pWT087 show statistically significant reduction in female cyst count ranging from 32.4% (WT87-L7) to 60.8% (WT87-L1) compared to susceptible control Williams 82.

TABLE 1

| | Event ID | | | | | |
|---|---|---|---|---|---|---|
| | W82 | CystX | AW30-L2 | WT87-L7 | WT87-L1 | WT87-L8 |
| AVG | 85.0 | 17.5 | 86.3 | 27.5 | 51.7 | 32.8 |
| Female index (%) | 100.0 | 20.6 | 101.5 | 32.4 | 60.8 | 38.5 |
| SE | 10.1 | 8.8 | 13.9 | 7.6 | 9.9 | 11.7 |
| n | 3 | 2 | 4 | 4 | 3 | 4 |

EXAMPLE 5

Molecular Characterization Of dsRNA Transgene Expression

To verify the expression of SCN target dsRNA and the production of small interfering RNAs (siRNAs) in hairy roots, a protocol has been developed to detect siRNAs in hairy roots. RNA samples in Formazol (Molecular Research Center, Cincinnati, Ohio) were run on a 15% acrylamide/bis (19:1)/7M urea gel in 1×Tris-borate/EDTA (TBE) at 200 volts (around 20 mA) for approximately 4 hours, or until the Bromophenol Blue dye was about 2 cm from the bottom of a 20 cm gel. The gel was transferred to Hybond-XL (Amersham Biosciences, Piscataway, N.J.) nylon membrane using a Trans-Blot Cell (Bio-Rad Laboratories, Hercules, Calif.) filled with 1×TBE at 500 mA (around 20 volts) for 2 hours. The membrane was then UV cross-linked. The bottom half of the membrane (below the xylene cyanol dye front) was hybridized with a $^{32}$P-labeled RNA probe that binds to the siRNAs of interest, and the top half was used as a loading control by probing with a $^{32}$P-labeled cDNA probe specific for soybean 5.8S rRNA. The RNA probe was made using Ambion's Maxiscript T7 kit (Ambion, Austin Tex.), using the manufacture's protocol. A DNase treatment was used after the transcription reaction, and the probe was passed sequentially through two NucAway spin columns (Ambion, Austin, Tex.) to remove unincorporated nucleotides. The probe was cleaved to an average size of 50 bases in carbonate buffer. To do this, 15 µl of carbonate buffer (0.67% sodium bicarbonate, 1.27% sodium carbonate (weight/volume)) was added per 1 µl of probe. The sample was incubated at 60° C. for a time dependent on the length of the probe, using the formula t=(Li−Lf)/(k×Li×Lf), where t=time in minutes, Li=initial length of probe in kb, Lf=final length of probe in kb, and k=rate constant=0.11 kb$^{-1}$min$^{-1}$. The reaction was neutralized with 1 µl 3M sodium acetate pH 5.0 per 15 µl of carbonate buffer. 2×10$^6$ counts per minute of radiolabeled probe was used per ml of hybridization solution.

As an example, RNA isolated from hairy root lines WT87L1, WT87L7, and WT87L8 was analyzed to detect siRNAs derived from *H. glycines* pas-5 using a $^{32}$P-labeled sense strand pas-5 RNA probe in the protocol described above. RNA isolated from the transgenic hairy root line AW30L1 containing DNA from the empty vector pAW30 was analyzed simultaneously as a negative control. *H. glycines* pas-5 siRNA was detected in hairy root lines WT87L1, WT87L7, and WT87L8, but not in hairy root line AW30L1. Similar amounts of total RNA were demonstrated to have been loaded in each well of the gel by hybridization with a $^{32}$P-radiolabeled 5.8S cDNA probe. The approximate size of the *H. glycines* pas-5 siRNA detected in RNA isolated from hairy root lines WT87L1, WT87L7, and WT87L8 was determined to be approximately 21 nucleotides by comparison to a RNA Decade ladder (Ambion, Austin Tex.) that was run on the same gel. Using similar methods, the presence of *H. glycines* pas-5 siRNA was confirmed for hairy root lines WT87L3, WT87L4, WT87L10, WT87L14, WT87L15, WT87L17, and WT87L18.

These results demonstrated that in soybean hairy-root, full-length dsRNA transgene for SCN target *H. glycines* pas-5 was processed into siRNA. SCN uses its feeding tubes to withdraw nutrients from host feeding cells (or syncytium). The unique structure of nematode feeding tubes limits the size of molecules (~20 kDa) that SCN can take up. The small size of the siRNA would allow SCN to take up these molecules.

What is claimed is:

1. An isolated expression vector comprising a nucleic acid encoding a double stranded RNA molecule comprising a first strand and a second strand complementary to the first strand, wherein the first strand is identical to a portion of a pas-5 target gene of a parasitic nematode, the portion
comprising from 19, 20, or 21 consecutive nucleotides to at least 400 consecutive nucleotides of SEQ ID NO: 1;
wherein the double stranded RNA inhibits expression of the pas-5 target gene.

2. An isolated expression vector comprising a nucleic acid encoding a multiplicity of RNA molecules each comprising a double stranded region having a length of at least 19, 20, or 21 nucleotides, wherein one strand of said double stranded region is obtained from SEQ ID NO: 1.

3. A transgenic plant capable of expressing at least one dsRNA comprising a first strand that is identical to a portion of a parasitic nematode pas-5 target gene and a second strand complementary to the first strand, wherein the first strand comprises at least 19, 20 or 21 consecutive nucleotides of SEQ ID NO: 1; and wherein the dsRNA inhibits expression of the plant parasitic nematode pas-5 target gene.

4. The transgenic plant of claim 3, which expresses a multiplicity of RNA molecules each comprising a double stranded region having a length of 19, 20, or 21 nucleotides.

5. The transgenic plant of claim 3, which is a soybean plant.

6. A method for controlling the infection of a plant by a parasitic nematode, the method comprising the step of contacting the nematode with a dsRNA molecule that comprises a first strand that is identical to a portion of a plant parasitic nematode pas-5 target gene and a second strand complementary to the first strand; and wherein the first strand comprises at least 19, 20 or 21 consecutive nucleotides of SEQ ID NO: 1.

7. A method of making a transgenic plant capable of expressing a dsRNA that is identical to a portion of a plant parasitic nematode pas-5 target gene, said method comprising the steps of:
a) preparing a nucleic acid having a first strand that is identical to the portion of the parasitic nematode pas-5 target gene and a second strand complementary to the first strand, wherein the nucleic acid is able to form a double-stranded RNA transcript once expressed in the plant, said first strand comprising from 19, 20, 21 consecutive nucleotides to 400 consecutive nucleotides of SEQ ID NO: 1.
b) transforming a recipient plant with said nucleic acid;
c) producing one or more offspring of said recipient plant; and
d) testing the offspring for expression of the double stranded RNA transcript.

8. The method of claim 7, wherein the first strand comprises 19, 20, or 21 consecutive nucleotides of SEQ ID NO: 1.

9. The method of claim 7, wherein the plant is a soybean plant.

10. The expression vector of claim 1, wherein the first strand comprises 19, 20, or 21 consecutive nucleotides of SEQ ID NO: 1.

11. The expression vector of claim 1, wherein the first strand comprises at least 50 consecutive nucleotides of SEQ ID NO: 1.

12. The expression vector of claim 1, wherein the first strand comprises at least 400 consecutive nucleotides of SEQ ID NO: 1.

13. The expression vector of claim 1, wherein the portion of the target gene is from nucleotides 73 to 589 of SEQ ID NO: 1.

14. The expression vector of claim 2, wherein the double stranded region comprises the sequence from nucleotides 73 to 589 of SEQ ID NO: 1.

15. The transgenic plant of claim 3, wherein the first strand of the dsRNA comprises nucleotides 73 to 589 of SEQ ID NO: 1.

16. The transgenic plant of claim 4, wherein the RNA molecules are obtained from nucleotides 73 to 589 of SEQ ID NO: 1.

17. The method of claim 6, wherein the first strand of the dsRNA comprises nucleotide 73 to nucleotide 589 of SEQ ID NO: 1.

18. The method of claim 7, wherein the first strand comprises nucleotide 73 to nucleotide 589 of SEQ ID NO: 1.

19. The method of claim 7, wherein the first strand is 19, 20, or 21 consecutive nucleotides of SEQ ID NO: 1.

20. The method of claim 7, wherein the first strand is at least 400 consecutive nucleotides of SEQ ID NO: 1.

* * * * *